(12) United States Patent
Malofsky et al.

(10) Patent No.: US 8,975,435 B2
(45) Date of Patent: Mar. 10, 2015

(54) METHYLIDENE MALONATE PROCESS

(75) Inventors: Bernard M. Malofsky, Bloomfield, CT (US); Chris Mariotti, Unionville, CT (US)

(73) Assignee: OpTmed, Inc., New York, NY (US)

( * ) Notice: Subject to any disclaimer, the term of this patent is extended or adjusted under 35 U.S.C. 154(b) by 0 days.

(21) Appl. No.: 12/774,810

(22) Filed: May 6, 2010

(65) Prior Publication Data

US 2010/0286438 A1 Nov. 11, 2010

Related U.S. Application Data

(60) Provisional application No. 61/215,610, filed on May 7, 2009, provisional application No. 61/215,578, filed on May 7, 2009, provisional application No. 61/291,898, filed on Jan. 3, 2010.

(51) Int. Cl.
*C07C 67/48* (2006.01)
*C07C 67/343* (2006.01)
*C07C 67/62* (2006.01)

(52) U.S. Cl.
CPC .............. *C07C 67/343* (2013.01); *C07C 67/62* (2013.01)
USPC ........................................... 560/191

(58) Field of Classification Search
None
See application file for complete search history.

(56) References Cited

U.S. PATENT DOCUMENTS

| | | | |
|---|---|---|---|
| 2,313,501 A | 3/1943 | Bachman et al. | |
| 2,330,033 A | 9/1943 | D'Alelio | |
| 3,197,318 A | 7/1965 | Halpern et al. | |
| 3,221,745 A | 12/1965 | Coover et al. | |
| 3,523,097 A | 8/1970 | Coover et al. | |
| 3,591,676 A | 7/1971 | Hawkins et al. | |
| 3,728,373 A * | 4/1973 | Imohel et al. | 558/381 |
| 3,758,550 A | 9/1973 | Eck et al. | |
| 4,049,698 A | 9/1977 | Hawkins et al. | |
| 4,056,543 A | 11/1977 | Ponticello | |
| 4,160,864 A | 7/1979 | Ponticello et al. | |
| 4,291,171 A | 9/1981 | Baum et al. | |
| 4,931,584 A | 6/1990 | Bru-Magniez et al. | |
| 5,142,098 A | 8/1992 | Bru-Magniez et al. | |
| 5,328,687 A | 7/1994 | Leung et al. | |
| 5,514,371 A | 5/1996 | Leung et al. | |
| 5,550,172 A | 8/1996 | Regula et al. | |
| 6,106,807 A | 8/2000 | Albayrak et al. | |
| 6,211,273 B1 | 4/2001 | Bru-Magniez et al. | |
| 6,420,468 B2 | 7/2002 | Bru-Magniez et al. | |
| 6,440,461 B1 | 8/2002 | Bru-Magniez et al. | |
| 6,512,023 B1 | 1/2003 | Malofsky et al. | |
| 6,610,078 B1 | 8/2003 | Bru-Magniez et al. | |
| 6,750,298 B1 | 6/2004 | Bru-Magniez et al. | |
| 8,609,885 B2 | 12/2013 | Malofsky et al. | |
| 2001/0034300 A1 * | 10/2001 | Yurugi et al. | 502/300 |
| 2004/0076601 A1 | 4/2004 | Bru-Magniez et al. | |
| 2013/0281580 A1 | 10/2013 | Malofsky et. al. | |

FOREIGN PATENT DOCUMENTS

JP 2008174494 A 7/2008

OTHER PUBLICATIONS

Diethyl Methylenemalonate. Wayne Feely et al. Organic Syntheses, Coll vol. 4, p. 298; vol. 38 p. 22 (1958).
Di-tert-Butyl Methylenemalonate. Paloma Ballesteros et al. Organic Syntheses, Coll. vol. 7, p. 142 (1990); vol. 64, p. 63 (1986).
2-Methylenedodecanoic Acid. C. Freeman Allen et al. Organic Syntheses, Coll. vol. 4, p. 616 (1963); vol. 38, p. 47 (1958).
Sustained delivery of growth factors from methylidene malonate 2.1.2-based polymers. Laurent Desire et al. Biomaterials 27 (2006) 2609-2620.
Biocompatible poly(methylidene malonate)-made materials for pharmaceutical and biomedical applications. Pascal Breton et al European Journal of Pharmaceutics and Biopharmaceutics XXX (2007)XXX-XXX.
Preparation and Characterization of Novel Poly(methylidene Malonate 2.1.2.)-made Nanoparticles Francois Lescure et al Pharmaceutical Research, vol. 11, No. 9, 1994, 1270-1277.
Synthesis and micellization of amphiphilic poly(ethylene oxide)-block-poly(methylidene malonate 2.1.2.) diblock copolymers. Virginie Larras et al Macromol, Rapid Commun. 2000,21,1089-1092.
Structure elucidation of methylidene malonate 2.1.2 cyclic trimers with mass spectrometry, liquid chromatography and nuclear magnetic resonance investigations. A. Salvador et al Journal of Pharmaceutical and Biomedical Analysis 22 (2000) 165-174.

* cited by examiner

*Primary Examiner* — Fereydoun G Sajjadi
*Assistant Examiner* — Jennifer C Sawyer
(74) *Attorney, Agent, or Firm* — Edward K. Welch, II; IP & L Solutions

(57) ABSTRACT

An improvement in the production of methylidene malonates is attained by use of specific reaction phase and/or separation phase polymerization inhibitors and combinations thereof.

34 Claims, No Drawings

METHYLIDENE MALONATE PROCESS

RELATED APPLICATION

This application is a non-provisional application and claims the benefit of U.S. Provisional Patent Application Ser. Nos. 61/215,610 and 61/215,578, both of which were filed on May 7, 2009 and entitled Improved Methylidene Malonate Process, and the benefit of U.S. Provisional Patent Application Ser. No. 61/291,898, filed Jan. 3, 2010, entitled Methylidene Malonate Process, all of which are hereby incorporated herein by reference in their entirety.

FIELD OF THE INVENTION

The present invention relates to an improved process for the production of methylidene malonates as well as the methylidene malonates produced thereby and the use thereof.

BACKGROUND

Methylidene malonates are compounds having the general formula (I):

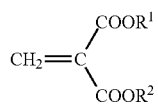

(I)

wherein $R^1$ and $R^2$ may be the same or different and represent H or a $C_1$ to $C_{18}$ hydrocarbon group or heterohydrocarbon group having one or more nitrogen, halogen, or oxygen atoms; provided that $R^1$ and $R^2$ are not both H. Such compounds have been known for well over half a century and their value in both organic synthesis and polymer chemistry is well known. Similarly, the use of these compounds as or as a component of adhesives, including skin bonding adhesive; molding materials; and the like is equally well known. Yet, despite all the promise, these compounds have found limited commercial success owing to the difficulty of their production; the poor, though improving, yet still erratic, yields; and the general instability of these compounds.

Numerous processes have been developed for the production of methylidene malonates having a formula similar to or falling within the formula of formula (I) above. Two of the earliest methods for the production of methylene dialkyl malonates, the simplest of the methylidene malonates, were the iodide method in which methylene iodide was reacted with dialkyl malonates and the formaldehyde method in which formaldehyde was reacted with dialkyl malonates in the presence of a base, in solution in alcohol solvents. The former was unsatisfactory due to very low yield and expensive starting materials. The latter, though periodically giving better yields than the iodide process, gave relatively poor yields and, more critically, was widely inconsistent from batch to batch, even under the same conditions.

Despite this inconsistency, early efforts continued to focus on the formaldehyde method. One of the most widely practiced formaldehyde methods consisted of reacting diethyl malonate with formaldehyde in glacial acetic acid in the presence of a metal acetate catalyst to produce the diethyl methylidene malonate. The latter was subsequently recovered by distillation following removal of the catalyst by filtration and separating off the solvent. These efforts continued to frustrate and various modifications and iterations of this basic process were developed all in an effort to improve the consistency and yields associated therewith.

Bachman et. al. (U.S. Pat. No. 2,313,501) taught the reaction of a $C_1$-$C_5$ dialkyl malonate with formaldehyde in the presence of an alkali metal salt of a carboxylic acid, in solution in a substantially anhydrous carboxylic acid solvent, followed by fractional distillation to separate the desired product. Bachman et. al. indicate that their process is advantageously carried out in the presence of inhibitors of the polymerization of monomeric vinyl compounds. Suitable inhibitors are said to include the copper salts such as copper chloride and, especially, copper salts of carboxylic acids such as cupric acetate, iron salts such as ferric acetate, and phenols, such as hydroquinone. These are added to the solution mix before the addition of the malonate.

Although Bachman et. al. reported yields of up to 72%, the results presented are conversion rates, not yields. Looking at the actual yields of the process, Bachman et. al.'s best performance was a yield of 43% with all others being less than 25%. Though Bachman et. al. speak of high purity and the ability to recover pure material, they never present any details or data as to what those purities or recoveries were. In any event, Bachman et. al. reported that the isolated product, upon standing, polymerized in a day to several weeks time depending upon the purity of the isolated material, which polymer was then heated to facilitate the reversion of the polymer to the monomer.

D'Alelio (U.S. Pat. No. 2,330,033), on the other hand, alleged that such processes were erratic and more often produced yields that averaged 10 to 12 percent. D'Alelio espoused an improved process with yields on the order of 30% and higher by reacting a malonic acid ester with formaldehyde in a ratio of one mole of the former to at least one mole of the latter under alkaline conditions and, in most cases, in the presence of a polymerization inhibitor such as copper, copper acetate, hydroquinone, resorcinol, or catechol, to form a methylol derivative. The methylol derivative is then acidified to a pH below 7.0 using a suitable organic or inorganic acid in order to retard further reaction. The acidified mass is then dehydrated to form the corresponding methylidene malonate which is subsequently separated by distillation.

Coover et. al. (U.S. Pat. No. 3,221,745 and U.S. Pat. No. 3,523,097) took another approach to the formation of the methylidene malonates, electing to begin with a preformed dialkyl alkoxymethylenemalonate. In accordance with their process, the olefinic double bond of the latter compound was subjected to hydrogenation in the presence of a hydrogenation catalyst and the hydrogenated compound was then subject to pyrolysis in the presence of a phosphorous pentoxide inhibitor to strip off the alcohol to produce the methylene malonate. The resultant mass was then subjected to vacuum distillation at low temperature to separate an allegedly high purity methylidene malonate, though with a low yield. According to Coover et. al., the use of low temperature distillation is said to prevent the contamination of the monomer with pyrolytic products that commonly result from high temperature distillation. These high purity monomers are said to be especially important for surgical applications.

In discussing the critical need for high purity materials, Coover et. al. draw particular attention to the extreme sensitivity of their monomers to the presence of even small amounts of acidic and basic impurities, the former inhibiting polymerization leading to sluggish and ineffective adhesive activity and the latter accelerating polymerization leading to unstable and useless products. They indicate that the amount of such impurities should not exceed 100 ppm, preferably not more than 10 ppm. Unfortunately, other than discussing its limitations with respect to the acidic and basic impurities, and despite its contention of high purity materials, Coover et. al. never provide any data pertaining to the purity of their materials. Clearly, though, these materials are not "pure" materials inasmuch as Coover et. al., like the others before them and since, require redistillation of the "pure" distillate.

Additionally, although suggesting that their high purity materials "have reasonably good" stability when stored in bulk, they recommend the addition of low levels, 0.0001 to 0.01 weight percent, of a polymerization inhibitor to the monomer materials in order to increase storage stability. Suitable polymerization inhibitors are said to include sulfur dioxide, hydroquinone, nitric oxide, organic acids, boron trifluoride, hydrogen fluoride, stannic chloride, ferric chloride, and organic anhydrides. To assist with cure, particularly cure speed, Coover et. al. also suggest the addition of cure accelerators or catalysts to their formulated adhesives, but cautions against adding them too early as they would cause premature polymerization.

Despite the erratic nature of the aforementioned processes, there were continued efforts to find improved processes for the production of methylidene malonates with a focus on more consistent and reliable processes with improved yields and higher purity. These effort focused not only on the simple methylidene malonates of the early art but also on finding new routes that allowed for the formation of a broader array of methylidene malonates, including symmetrical and asymmetrical species as well as those whose ester functionality was more complex, e.g., having a higher carbon number, unsaturation, heteroatoms and the like.

Eventually, such efforts led to multi-step processes in which certain unsaturated molecules served as a platform for the formation of intermediate adducts from which the methylidene malonates were subsequently stripped and recovered. For example, Hawkins et. al. (U.S. Pat. No. 4,049,698) found that certain malonic diesters could be reacted with formaldehyde and a linear, conjugated diene in the presence of a primary, secondary or tertiary amine at about reflux temperature to form an intermediate adduct that could then be readily pyrolyzed at temperatures in excess of 600° C. to split off the desired methylidene malonate. Similarly, Ponticello (U.S. Pat. No. 4,056,543) and Ponticello et. al. (U.S. Pat. No. 4,160,864) developed processes by which asymmetrical methylene malonates, especially methyl allyl methylene malonate, were prepared from previously formed norbornene adducts, the latter having been prepared by the Diels-Alder reaction of an alkyl acrylate with cyclopentadiene at room temperature or with heating or use of a Lewis catalyst. The so formed monoester norbornene adducts were then reacted with an electrophile material in the presence of an alkyl-substituted lithium amide complex to form the diester adduct and subsequently pyrolyzed at a temperature of 400° C. to 800° C. at a pressure of 1 mm to 760 mm Hg in an inert atmosphere to strip off the desired methylene malonates. These efforts, despite their gains in yield and/or purity, still failed to achieve commercial success.

Citing numerous disadvantages of the foregoing processes, which disadvantages were said to make them difficult, if not impossible, to adapt to industrial scale, Bru-Magniez et. al. (U.S. Pat. No. 4,932,584 and U.S. Pat. No. 5,142,098) developed a process whereby anthracene adducts were prepared by reacting mono- or di-malonic acid ester with formaldehyde in the presence of anthracene, most preferably in a non-aqueous solvent medium in the presence of select catalysts. According to Bru-Magniez et. al., the anthracene adducts were said to be readily produced in high yields with the desired methylidene malonates obtained by stripping them from the anthracene adduct by any of the known methods including heat treatment, thermolysis, pyrolysis or hydrolysis; preferably heat treatment in the presence of maleic anhydride. The resultant crude products were then subjected to multiple distillations, preferably lower temperature distillations under vacuum, to recover the purified methylidene malonate. Despite the claim to high yields, their crude yields were generally in the range of 21-71%, more importantly, nothing is said with respect to the purity of the material obtained.

Based on conversations with the successors to the Bru-Magniez technology, efforts to commercially produce the material have met with great difficulty owing to the high instability of the overall production process and final products. Indeed, they reported a high failure rate: of the limited batches that actually survived through crude distillation, the resultant products had to be stored in a freezer even after stabilizing with upwards of 50,000 ppm $SO_2$ due to their high instability and spontaneous polymerization. Indeed, our own attempts to follow the prior art processes, including the Bru-Magniez process, most often resulted in failure owing to sublimation of the paraformaldehyde, a failure to produce the desired product (as evidenced by a lack of double bonds in the reaction product), and, more frequently, polymerization of the reaction mix and/or the crude yield. Even when a successful run was realized, it has now been found that the purity of the materials was quite low. Though the traditional analytical tests employed, including, the boiling point, fraction temperature, and refractive index suggests good yield and purity, further, more sophisticated analysis has found that these reaction products actually contained a number of analogs of the desired methylidene malonate, in addition to the desired material, as well as various byproducts. For example, in our efforts to produce 1-ethoxycarbonyl-1-ethoxycarbonyl methylene oxycarbonyl ethane (the 2.1.2 monomer), we found that besides the 2.1.2 monomer, the reaction products, even after initial separation and distillation, contained substantial amounts of the di-substituted and unsubstituted analogs (the 2.1.1.2 and 2.2 analogs, respectively) and oligomers and polymers of the foregoing, as well as various byproducts, especially glutarates. Consequently, though yields were presumably higher than achieved by other methods, purity was not as high as hoped and, as found through subsequent effort, repeatability was erratic at best.

While these advances in the art promoted somewhat higher yields and greater versatility, particularly with respect to the broader variety methylidene malonates, lingering problems persisted, namely batch-to-batch inconsistency, if not outright failure, and the general instability of the subsequent isolation and purification efforts and, for those products that survived, the instability of the so-formed products, especially in bulk storage, and of formulated products, such as adhesives, made with the same.

Due to the inherent problems with instability of the isolation and purification processes, focus instead seemed to focus on efforts to stabilize whatever products were recovered as well as formulated products containing those recovered monomers. For example, Ponticello and Ponticello et. al. suggested that the resulting products could be better stabilized by the addition of certain acidic polymerization inhibitors such as sulfur dioxide, hydrogen fluoride, boron trifluoride, nitric oxide, organic acids, organic anhydrides, stannic chloride and ferric chloride or certain free radical inhibitors such as hydroquinone, catechol, and monomethyl ether of hydroquinone. Although the aforementioned Bru-Magniez et. al. patents did not discuss the inclusion of polymerization inhibitors in their isolated monomer, a review of their subsequent patents demonstrating the utilization of the so formed methylidene malonates made clear that they too employed SO$_2$ as a polymerization inhibitor of the formed methylidene malonates: a fact subsequently confirm in personal conversations with the successors to the Bru-Magniez technology. For example, Bru-Magniez et. al. (U.S. Pat. No. 6,640,461; U.S. Pat. No. 6,610,078; and U.S. Pat. No. 6,750,298) all speak of the need to degas the monomer under vacuum to remove the polymerization inhibitor SO$_2$. Malofsky et. al. (U.S. Pat. No. 6,512,023) theorized that the stability of 1,1-disubstituted ethylene monomer and polymers could be improved by the use of specific combinations of certain vapor phase and certain liquid phase anionic polymerization inhibitors. While methylidene malonates fall within that broad class of materials, Malofsky et. al. only demonstrated and, in the prosecution of their patent, argued specificity and uniqueness of their solution to cyanoacrylate monomers and monomer compositions, distinguishing over efforts to stabilize the production of the monomers as well as other monomers.

While Bru-Magniez et. al. certainly achieved many benefits and made significant advances in the production of methylidene malonates and while the addition of the high levels of SO$_2$ polymerization inhibitor to the isolated methylidene malonates and products containing them led to improved bulk storage stability and overall formulated product stability, freezer storage was still required, or strongly recommended, and Bru-Magniez' enthusiasm and accolades relative to industrial scale production were soon found to be tempered by continued inconsistency and instability in production as well as yields that, while higher, were still commercially undesirable, if not unviable. For example, Regula et. al., (U.S. Pat. No. 5,550,172), seemingly in endeavoring to follow the teachings of Bru-Magniez et. al., were only able to attain yields of less than 60 percent based on the adduct, though of high purity. Similarly, our own efforts to duplicate the results attained by Bru-Magniez et. al., even on a bench scale, resulted in wide variation in yields with very few attempts achieving or even coming close to those recited in Bru-Magniez. Indeed, on many occasions our efforts failed altogether due to the in-situ polymerization of the reaction mix in the reactor vessel.

Consequently, despite all the efforts and advances made in the art and the apparent desirability for these materials, no one has yet been able to adequately address the underlying and critical problems of process instability and inconsistency in the production of the methylidene malonates. It is this erratic nature of the production process and the attendant costs associated therewith that compromises and overshadows the commercial value and opportunity for these products.

Thus, if the methylidene malonates are ever to realize their commercial potential and promise, particularly in applications other than niche, high value added applications whose pricing can better offset the losses, costs and low yields of current processes, improved processes must be developed, especially processes that provide for more consistent and predictable yields. However, it has also been found that yield alone is not sufficient. Indeed, it has now been found that purity of the monomer, purity that goes far beyond the concerns with acidic and basic impurities as forewarned by Coover et. al., plays an important role in the cure or polymerizable characteristics of these materials and, perhaps most importantly, the properties of the polymerized materials. This is especially true for adhesive type applications for these materials.

Thus, there is a need for processes for the production of methylidene malonates that are not fraught with process failures, widely varying yields, unstable products, and unintended polymerizations and other by-products.

Furthermore, there remains a need in the industry for improved processes for the production of methylidene malonates wherein the formation of byproducts, such as glutarates, and dimers, oligomers and polymers of the methylidene malonates as well as thermal degradation products of the foregoing and the starting reactants, are lessened, if not avoided, particularly during the separation and fractionation steps for the recovery of the methylidene malonates.

In particular there is a need for a process that consistently achieves crude yields in excess of 35%, preferably in excess of 45%, more preferably in excess of 50%, especially with purities of the desired product and its analogs on the order of 80%, preferably 90% or more. Indeed, it would be phenomenal to attain purified yields on the order of 30% or more, let alone 40% or more, wherein the resultant product contained less than 8%, preferably less than 6%, most preferably less than 4%, of impurities and less than 12%, preferably less than 10%, most preferably less than 8% of the analogs of the desired product, on a consistent basis, and most preferably without the use of an intermediate adduct. Furthermore, such products would realize their true capabilities if one could produce the same on a commercial scale at a cost comparable to that for the production of cyanoacrylate monomer, in terms of actual costs, yields and/or purity.

Similarly, and in following therewith, there is a ongoing need for methylidene malonates whose bulk and long term storage stabilization is attained without concern for, or certainly less concern with respect to, the impact of such stabilization on the subsequent polymerization characteristics of the so formed methylidene malonates and which can be stored at room temperature. In particular, there remains a need and desire for methylidene malonates that do not require low temperature storage and/or further processing, such as degassing or the addition of scavengers, to remove stabilizers and polymerization inhibitors before the methylidene malonates can be formulated into end-use products and/or used in their intended end-use applications.

Finally, there is a need and desire for methylidene malonates that do not require, or require less, catalyst, polymerization activator and/or accelerator and the like, than heretofore required, in order to attain a sufficient degree and/or speed of polymerization, especially in adhesive and like bonding applications.

SUMMARY OF THE INVENTION

The present invention provides for improved processes for the production of methylidene malonates and for the purification and isolation thereof as well as for the methylidene malonates formed thereby. Specifically it has now been found that the addition of one or more polymerization inhibitors, the "reaction phase polymerization inhibitors", to the reaction mix containing the intermediate malonate adduct prior to or concurrent with the stripping step greatly reduces if not eliminates the instability of the process and the resultant products enabling more consistent and predictable processes with high yields of methylidene malonates. Similarly, it has also been found that the addition of the same or different polymerization inhibitors, the "separation phase polymerization inhibitors", to a methylidene malonate crude product or partially purified product prior to or concurrent with those steps employed to separate and/or isolate the methylidene malonate, as well as to the separated or collected products themselves, preferably to the collection vessels for the purified materials prior to the collection, greatly improves the stability of the same. In its most preferred embodiment, the one or more polymerization inhibitors, whether reaction phase or separation phase, comprise at least one anionic polymerization inhibitor in combination with one or more free radical polymerization inhibitor.

According to a first aspect of the present invention the improved process comprises a two-step process in which a malonic acid ester is reacted with formaldehyde or a formaldehyde source in the presence of a diene or suitable polynuclear aromatic compound or platform to form the associated malonate adduct and the adduct is then subjected to a stripping step in which the methylidene malonate is stripped from the platform, wherein the improvement comprises the addition of one or more reaction phase polymerization inhibitors to the formed malonate adduct concurrent with or prior to the stripping step. An especially preferred embodiment is that wherein the platform is cyclopentadiene or anthracene and the one or more reaction phase polymerization inhibitors comprises at least one anionic polymerization inhibitor in combination with one or more free radical polymerization inhibitor.

According to a second aspect of the present invention the improved process comprises a one-step process in which a preformed malonate adduct, especially one based on a diene or polynuclear aromatic platform, is subjected to a stripping step in which the methylidene malonate is stripped from the adduct platform wherein the improvement comprises the addition of one or more reaction phase polymerization inhibitors to the malonate adduct concurrent with or prior to the stripping step. An especially preferred embodiment is that wherein the platform is either cyclopentadiene or anthracene and the one or more reaction phase polymerization inhibitors comprises at least one anionic polymerization inhibitor in combination with one or more free radical polymerization inhibitor.

In accordance with the foregoing embodiments, it is to be appreciated that each process may include additional steps wherein the malonate adduct or malonate precursor thereto is subjected to one or more reactions by which one or both of the ester groups of the "malonate" portion of the adduct or precursor is removed, replaced, or modified. For example, one or both ester groups could be replaced with a higher carbon number hydrocarbyl group, with a hydrocarbyl group different from the other, with a reactive or functional heteroatom or heteroatom-containing radical and the like. With respect to the latter one or both ester groups could be modified or replaced to include an ether, ester, aldehyde, ketone, cyano, aryl, halo or epoxide group.

Furthermore, it is to be appreciated that additional reaction phase stabilizer, or as discussed below, a separation phase stabilizer will be added to the reaction product of either of the foregoing processes should the crude product or the isolated crude liquid product be stored before further efforts are undertaken to isolate and purify the methylidene malonate. In this regard, it is understood that the crude product of the foregoing processes will be subjected to one or more separation and/or purification steps or processes, most preferably by separation and/or crude distillation followed by a plurality of fractionation or distillation steps, depending upon the purity attained and/or desired or needed.

Thus, according to a third aspect of the present invention there is provided an improved process for the separation and isolation, i.e., the purification, of methylidene malonates wherein the improvement comprises the addition of a separation phase polymerization inhibitor to the materials to be subjected to the various separation or purification steps as well as, preferably, the collected materials from each of those steps. The separation phase polymerization inhibitor may be the same as the reaction phase polymerization inhibitor or a different polymerization inhibitor system comprising components suitable for use as reaction phase polymerization inhibitors or it may comprise at least one secondary anionic polymerization inhibitor, alone or in combination with one or more free radical polymerization inhibitors. As with the reaction phase polymerization inhibitor, the separation phase polymerization inhibitor system preferably comprises at least one liquid phase anionic polymerization inhibitor alone or, more preferably, in combination with one or more free radical polymerization inhibitors.

While the separation phase polymerization inhibitor is added to the crude or partially purified materials to be further purified, the same or a different separation phase polymerization inhibitor may also be, and is preferably, added to the collected material arising from each separation or fractionation process following its collection. Most preferably, a portion of the latter separation phase polymerization inhibitor is to be added to the collection flask or vessel prior to initiation of the separation process and the remainder added to the collected material following completion of the collection. The amount of the separation phase polymerization inhibitor system to be added to the empty collection flask or vessel will be based on the theoretical or projected amount of material to be collected (or a substantial portion thereof): generally the amount will be somewhat less than that needed if the full amount projected to be recovered were to actually be recovered. Once the separation is completed, the amount of separation phase polymerization inhibitor is then adjusted upward, as appropriate, based on the actual amount collected. This same process, i.e., the addition of the separation phase polymerization inhibitor system, will be used for each successive separation or purification step employed, if any.

In yet a fourth aspect of the present invention, there is provided an improved overall process for the production and recovery of methylidene malonates, from malonate adduct (or malonate precursor in the case of the two-step process) to purified methylidene malonate, which process employs both a reaction phase polymerization inhibitor system in the reaction phase or stripping step of the methylidene malonate production process and a separation phase polymerization inhibitor system in the separation, purification, and recovery phase of the methylidene malonate production process.

By implementing the improved processes as set forth herein, one realizes more consistent and improved yields. For example, one may attain crude yields in excess of 35%, preferably in excess of 45%, more preferably in excess of 50%, most preferably in excess of 60% or more, even 70 or 80% or more, on a consistent and repeatable basis. Most importantly, these yields are attained with a concomitant high purity, generally 60% or more, preferably 75% or more, more preferably 80% or more, most preferably 90% or more.

Furthermore, one may achieve even higher purities, with only minimal or modest loss in yield, but still excellent yields, by the further fractionation of the partially purified products attained by the improved separation processes. Generally, one is able to realize purified yields in excess of 20%, preferably in excess of 30%, more preferably in excess of 35%, most preferably of about 40% or more, based on the theoretical yield possible from the original malonate adduct, on a repeatable and consistent basis. Furthermore, these "purified" fractions or collections of methylidene malonate generally have purities exceeding 80%, preferably 85%, more preferably 90%, most preferably 95%. Thus, even if the yields, especially the purified yields, slip below the aforementioned targets, the loss in yield is more than made up for by the increased purity attained with the improved processes. Hence; yields as low as 15%, even 10%, with high purity of 85% or higher, preferably 90% or higher, most preferably 95% or higher, provides a suitable process and is within the scope of the present invention. Generally speaking, the improved processes of the present invention provide for high purity wherein the purified product contains less than 8%, preferably less than 6%, most preferably less than 4%, of impurities and less than 12%, preferably less than 10%, most preferably less than 8% of the analogs of the desired product, on a consistent basis.

In accordance with another aspect of the present invention there are provided stable, high purity methylidene malonates, in crude and/or purified form, produced by any of the foregoing improved methods. In particular, there are provided stable, high purity methylidene malonates comprising the methylidene malonate and an effective amount of a polymerization inhibitor combination of at least one anionic polymerization inhibitor and one or more free radical polymerization inhibitor.

Finally, in accordance with yet another aspect of the present invention there are provided methylidene malonate adhesive compositions comprising the methylidene malonates prepared in accordance with the foregoing processes.

DETAILED DESCRIPTION

As used herein and in the appended claims, herein the term "crude product" or "crude yield" means that reaction product containing the intended methylidene malonate subsequent to the striping of the methylidene malonate from the adduct and prior to any separation or isolation steps to remove the non-liquid components, e.g., residue of the maleic acid and/or the platform molecule of the adduct. As context allows, it may also mean that liquid reaction product remaining after separation, whether by filtration, crude distillation or the like, of the liquid materials from the solids in the reaction product mix: although this is oftentimes referred to as the crude liquid product. Also, as used herein the term "initial re-distillation" or "second distillation" refers to the initial distillation of the crude yield, i.e., liquid monomer distilled from or otherwise separated from the reaction mix. The term "fractionation" is used herein to mean the act or process of separating, isolating and/or purifying the methylidene malonate from the liquid phase of the crude reaction product, most notably, from the crude liquid reaction product, as well as any subsequent steps or processes to further increase the purity thereof. Further, when referencing the amount of polymerization inhibitors to be used, the amount is presented in parts per million (ppm) based on the weight of the malonate adduct (unless otherwise indicated) in the case of the reaction phase polymerization inhibitors and on the theoretical weight of the recoverable methylidene malonate in the case of the separation phase polymerization inhibitors, unless otherwise indicated. Finally, it is to be noted that the terms "stabilizer" and "polymerization inhibitor" are used interchangeably herein: each having the same intended definition.

Methylidene malonates are compounds having the general structure (I):

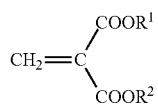

(I)

wherein $R^1$ and $R^2$ may be the same or different and represent H or a $C_1$ to $C_{18}$ hydrocarbon group or heterohydrocarbon group having one or more nitrogen, halogen, or oxygen atoms; provided that $R^1$ and $R^2$ are not both H. Preferably each $R^1$ and $R^2$ are each independently a $C_1$ to $C_{10}$, most preferably a $C_1$ to $C_6$, linear or branched alkyl group; a $C_3$ to $C_6$ alicyclic group; a $C_2$ to $C_6$ alkenyl group; or a $C_2$ to $C_6$ alkynyl group; any of which may optionally be substituted with an ether, epoxide, halo, ester, cyano, aldehyde, ketone or aryl group. A further preferred subset of methylidene malonates are those wherein one or both of $R^1$ and $R^2$, which may be the same or different, are of the formula (IV):

(IV)

wherein $R^8$ is a $C_1$ to $C_6$ lower alkyl and n is an integer of from 1 to 5, said ester group most preferably having been formed as a result of an ester exchange reaction.

The improved process of the present invention may be adapted to/adopted for use in any of the conventional methods for the production of methylidene malonates involving the formation of or starting with a malonate adduct wherein the desired methylidene malonate is stripped from the malonate adduct. Specifically, it has now been found that one may markedly and surprisingly improve the yield, stability and/or predictability of these prior art methods as a result of the use of certain polymerization inhibitors prior to or concurrent with the stripping step in which the methylidene malonate is stripped from the malonate adduct In accordance with the first embodiment of the present invention, there is provided an improved "two-step process" for the production of the methylidene malonates wherein the improvement lies in the fact that the stripping step is conducted in the presence of a reaction phase polymerization inhibitor. The two-step process generally refers to that process in which one first prepares the intermediate malonate adduct and then proceeds with the stripping step. Specifically, the two-step process generally comprises the steps of reacting a malonic acid ester, preferably the diester, with formaldehyde in the presence of a diene or polynuclear aromatic platform to form the malonate adduct and, sequentially or at some later point thereafter, subjecting the so formed or further modified adduct to a stripping process by which the methylidene malonate is stripped from the platform in the presence of the reaction phase polymerization inhibitor.

As noted, the two-step process typically involves an initial Diels-Alder reaction between a malonic acid ester and formaldehyde in the presence of a suitable conjugated diene or polynuclear aromatic platform. Malonic acid esters are generally of the formula (VI)

(VI)

wherein $R^{11}$ and $R^{12}$ may be the same or different and represent H or a $C_1$ to $C_{18}$, preferably a $C_1$ to $C_{10}$, most preferably a $C_1$ to $C_6$, linear or branched alkyl group; a $C_3$ to $C_6$ alicyclic group; a $C_2$ to $C_6$ alkenyl group; or a $C_2$ to $C_6$ alkynyl group, but $R^{11}$ and $R^{12}$ are not both H. Additionally, either or both of the aforementioned $R^{11}$ and $R^{12}$ groups may be substituted with an ether, epoxide, halo, ester, cyano, aldehyde, ketone or aryl group, especially desirable are those wherein at least one of the $R^{11}$ and $R^{12}$ groups is of the formula (IV):

(IV)

wherein $R^8$ is a $C_1$ to $C_6$, preferably a $C_1$ to $C_3$, lower alkyl and n is an integer of from 1 to 5, preferably 1 or 2. The acid may be a monoester or a diester, but is preferably a diester. Exemplary malonic acid esters include dimethyl malonate, diethylmalonate, diisopropyl malonate, di-n-propyl malonate, and ethyl methyl malonate as well as those wherein one of $R^{11}$ and $R^{12}$ is $—(CH_2)_n—COOR^8$ wherein $R^8$ is a $C_1$ to $C_3$ lower alkyl and n is 1 or 2.

As used herein the term "formaldehyde" refers to formaldehyde as well as to any source of the compound having the formula H—C(O)—H such as paraformaldehyde, formalin, gaseous formaldehyde and the like.

As used herein the term "diene" refers to conjugated diene platforms. These include the linear conjugated diene compounds corresponding to the following formula:

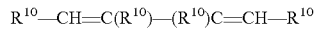

$$R^{10}—CH=C(R^{10})—(R^{10})C=CH—R^{10}$$

wherein each $R^{10}$ is independently hydrogen, methyl or ethyl as well as the corresponding alicyclic dienes. Suitable dienes include 2-methyl-1,3-pentadiene, 1,3-hexadiene, cyclopentadiene, isoprene, 1,3-butadiene, 2,4-hexadiene, 2,3-dimethyl-1,3-butadiene, etc.

"Polynuclear aromatic compounds" are compounds that have multiple, fused, six-membered rings, all or most of which are aromatic rings, especially those of the benzenoid type. Such compounds are also well known. Preferred polynuclear aromatic platforms include anthracene, naphthalene, naphthacene, and phenanthrene, most especially anthracene.

The reaction conditions as well as other constituents that may be present in the formation of the malonate adducts, including solvents, catalysts, etc. and their amounts, are all well known in the art and will be further discussed below.

Generally speaking, when preparing the malonate adduct, the conjugated diene or polynuclear aromatic platform is typically present in about an equimolar amount to a slight molar excess, preferably from about 1.0× to 1.4×, most preferably a 1.0 to 1.2×, molar excess relative to the malonic acid ester, whereas formaldehyde or the formaldehyde source and malonic acid ester are generally combined in equimolar or near equimolar amounts. The reaction is generally conducted at reflux temperature, e.g., about 50° C. to about 110° C., preferably from about 70° C. to about 90° C., to form the adduct mixture. Water formed by this process may be azeotroped out with the excess diene or aromatic compound.

The initial step, i.e., the reaction of the formaldehyde with the malonic acid in the presence of the platform material, is preferably conducted in a suitable solvent, preferably a non-aqueous solvent, in the presence of a catalyst. Such catalysts are generally present at from 0.1 to about 10 weight percent based on the weight of the malonate ester.

Suitable catalysts include primary, secondary and tertiary amines, especially secondary aliphatic amines; particularly where the platform is a conjugated diene. Exemplary amine catalysts include piperidene, piperazine, N-methylpiperazine, dibutylamine, morpholine, diethylamine, pyridine, triethylamine, tripropylamine, triethylenediamine, N,N-dimethylpiperazine, butylamine, pentylamine, hexylamine, heptylamine, nonylamine, decylamine, and the like. Especially preferred amines include piperidene, piperazine, N-methylpiperazine, dibutylamine, morpholine, and diethylamine. The salts of these amines with organic monocarboxylic acids, such as piperidine acetate, also act as effective catalysts.

Alternatively, where the platform is a polynuclear aromatic compound, the catalyst is preferably a metal salt of a lower monocarboxylic acid such as copper(II) acetate, cupric acetate monohydrate, potassium acetate, zinc acetate, zinc chloracetate, magnesium chloracetate, magnesium acetate, and combinations of any two or more thereof, especially copper(II) acetate, potassium acetate and combinations of the two.

Although non-aqueous solvents are preferred, the reactions may be conducted in either an aqueous or a non-aqueous medium. Advantageously, the non-aqueous medium may be a water miscible solvent, a water immiscible solvent, or a combination of at least one water miscible solvent and at least one water immiscible solvent: the choice being dependent upon the particular system and materials employed. Exemplary non-aqueous solvents include, but are not limited to, acetic acid, acetic anhydride, glacial acetic acid, benzene, bromobenzene, xylene, toluene, dimethylformamide (DMF), dimethylsulfoxide (DMSO), tetrahydrofuran, a ketone such as dimethyl ketone or ethylmethyl ketone, alkanes such as heptane to hexane, acetonitrile, dioxane, N-methylpyrrolidone (NMP) or combinations of any two or more of the foregoing. Exemplary combinations include, but are not limited to glacial acetic acid/xylene, benzene/acetic acid, xylene/acetic acid/acetic anhydride, dimethyl ketone/acetic acid, ethylmethyl ketone/acetic acid, acetonitrile/acetic acid and the like.

The resultant product of this initial step is an intermediate malonate adduct which has the following structure (VII):

(VII)

incorporated into or bonded to the platform species, most often incorporated into a ring structure with the diene or as a pendant ring to the pre-existing ring structure of an alicyclic diene or polynuclear aromatic compound. For example, when the conjugated diene is a linear conjugated diene, the malonate adduct will have a single ring structure with the above structure (IV) forming part of that ring. On the other hand, when the conjugated diene is cyclopentadiene or the polynuclear aromatic compound anthracene the structure (IV) forms a pendant ring to the existing rings, e.g., the former results in a norbornene ring structure. Such intermediate malonate adducts and their formation are disclosed in the aforementioned Hawkins et. al., Ponticello, Ponticello et. al. and Bru-Magniez patents.

The resultant reaction mix comprising the malonate adduct may then be subjected to filtration or another separation process to remove components thereof that may interfere with the stripping of the methylidene malonate. For example, if catalysts are employed in the adduct formation or in any other subsequent reactions involving the initial adduct, e.g., in any transesterification reaction, hemihydrolysis, etc., prior to the stripping step, it is necessary to filter out any catalyst materials. Similarly, depending upon the solvents used in those processes, it may be desirable to employ separation steps to isolate the adduct or at least remove some of the solvent(s). Otherwise, and once the adduct is isolated, the adduct is then subjected to a stripping process to recover the methylidene malonate or it may first be subjected to any number of alternative processes for removing and/or altering the ester groups, as mentioned above. For example, again as mentioned above, the formed malonate adduct may be subjected to hemihydrolysis and subsequent alkylation to form an asymmetrical malonate adduct. Other processes and reactions for forming other malonate adducts having symmetrical or asymmetrical ester groups, higher carbon number ester groups and/or hetero atom containing ester groups are all known in the art.

Finally, the desired intermediate malonate adduct of the two-step process or, in the case of the "one-step process," a preformed malonate adduct is then subjected to the stripping process by which the methylidene malonate is stripped from the diene or polynuclear aromatic platform wherein, in accordance with the present invention, said stripping is conducted in the presence of the reaction phase polymerization inhibitor. Where a preformed malonate adduct is employed, the malonate adduct may have been made by any of the methods known in the art, including, but not limited to, the two-step processes mentioned above, as well as by similar reactions in which, for example, alkyl acrylates are reacted with a diene or polynuclear aromatic platform, as disclosed in Ponticello et. al. The formation of such malonate adducts is well know, as are the reaction conditions and other co-constituents such as catalysts, solvents and the like. Furthermore, certain of these malonate adducts are commercially available from Virsol of Paris, France.

Stripping of the methylidene malonate form the adduct may be accomplished by any of the known methods including heat treatment, thermolysis, pyrolysis, and hydrolysis. These methods and the associated equipment needs are well known in the art. Most preferably, the stripping is desirably attained by use of the least costly and egregious method capable with the specific malonate adduct. In a most preferred embodiment, especially those wherein the platform is cyclopentadiene or anthracene, the stripping is conducted with a heat treatment in the presence of a suitable stripping agent, namely an agent known in the art suitable for reversing the Diels-Alder reaction, especially maleic anhydride, in an appropriate solvent or other medium or diluent, and, most importantly in the presence of the reaction phase polymerization inhibitor.

When maleic anhydride or another suitable stripping agent is employed, it is present in at least a near equimolar, preferably an equimolar amount, to a molar excess amount based on the moles of adduct or intermediate adduct. Generally, the amount of maleic anhydride or other suitable stripping agent will be from about 0.8× to about 2×, preferably from about 1× to 1.5×, most preferably >1× to 1.3×, the number of moles of adduct or adduct intermediate. Higher or lower amounts could also be used; but higher amounts will just add cost and waste whereas lower amount will result in reduced yields and/or slower reactions.

As known in the art, the stripping reaction is preferably carried out in a suitable solvent or medium. Exemplary media include paraffin oil, mineral oil, tricresyl phosphate and the like. The specific solvent selection is more a matter of personal preference and the process conditions employed. However, it has also been found that certain media, such as tricresyl phosphate, may be advantageously employed due to the fact that they do not, or have a lesser tendency to, carry over into the distillate during distillation. This avoids or at least lessens the need to employ intermediate separation, especially solvent separation, steps in the distillation process.

In all of the aforementioned processes, it is to be appreciated and understood that the number of steps recited, namely the "two-step process" or the "one-step process" refers only to the adduct formation and stripping steps. Typically the production of methylidene malonates can, and most preferably does, involve other process steps for the production and/or isolation of the ultimately desired methylidene malonate compounds.

In this regard, it is to be appreciated that improved processes for the production of the methylidene malonates according to the present invention may further comprise any number of additional steps whereby the malonate adduct, in either process, or, in the case of the two-step process, the malonate precursor is subjected to one or more additional reactions by which one or both of the ester groups of the malonate or precursor is removed, replaced, and/or modified. Such reactions enable one to tailor the final structure and functionality of the methylidene malonate to be produced. For example, such processes allow one to substitute one or both ester groups with different hydrocarbyl groups, typically higher carbon number hydrocarbyl groups: the former enabling the production of asymmetrical methylidene malonates and the latter most preferably producing methylidene malonates of higher carbon number. Similarly, such reactions may be employed to modify or substitute one or both ester groups with an ester group incorporating any number of reactive or functional groups or radicals or with an alternate reactive or functional group altogether. For example, the ester may be modified or substituted with or replaced by a further reactive or functional group or a non-functional group, including, e.g., an ether, epoxide, halo, ester, cyano, aldehyde, ketone or aryl group. Further, such groups or moieties could be functional or reactive groups or moieties for subsequent cross-linking and/or co-polymerization of the methylidene malonates with itself or, preferably, with other monomers, compounds, reactants, cross-linkers, hardeners, etc.

Suitable methods for accomplishing the foregoing are well known. For example, monoesters can be prepared from the dialkyl adducts by reacting the same with an alkali metal or alkaline earth metal salt, especially sodium or potassium hydroxide, in an alcoholic solvent. Similarly, asymmetric compounds may readily be prepared from the monoester addition product by reaction with a halogen-containing product whose radical is to form a second ester radical which is different from the first ester radical. Transesterification is an especially desirable method by which such asymmetrical or heteroatom-containing compounds are formed. Such processes are described in, for example, Hawkins et. al. (U.S. Pat. No. 4,049,698), Ponticello (U.S. Pat. No. 4,056,543), Ponticello et. al. (U.S. Pat. No. 4,160,864), and Bru-Magniez et. al. (U.S. Pat. No. 4,932,584 and U.S. Pat. No. 5,142,098), all of which are hereby incorporated herein in their entirety by reference.

Notwithstanding the foregoing, perhaps the most important of these additional steps or processes is that by which the methylidene malonate is actually recovered from the resultant product of the stripping process. Specifically, the products of the stripping process must undergo one or more sequential separation and/or distillation steps to isolate the stripped materials from the adduct platform and any solvent or reaction medium. Most preferably, in accordance with a third aspect of the present invention, the overall process further comprises additional separation, distillation and/or fractionation steps, the purification process, to isolate and purify the desired methylidene malonate from the crude product.

Thus, according to a third aspect of the present invention, there is provided an improved process for the separation, purification, and isolation of methylidene malonates from the crude reaction product, before or, preferably, after, separation of the crude liquid reaction product from the overall reaction product, wherein the improvement comprises the addition of a separation phase stabilizer system to the recovered fractions, i.e., the separated or purified methylidene malonate material. Like the reaction phase stabilizer system, the separation phase stabilizer system comprises one or more anionic polymerization inhibitors, at least one of which must be a liquid phase anionic polymerization inhibitor, alone or in combination with at least one free radical polymerization inhibitor. However, unlike the reaction phase stabilizer system, the anionic polymerization inhibitor(s) of the separation phase stabilizer system may be just secondary anionic polymerization inhibitors. Additionally, in those situations where the fractionation process is merely a continuation of the reaction process discussed above (i.e., the two-step process), one may optionally employ the reaction phase stabilizer system as the separation phase stabilizer system, at least for stabilization of the crude product or, if separated, the crude liquid product. Generally, though, the reaction phase stabilizer system and the separation phase stabilizer system will be different, especially in the collected materials from each aspect of the purification process. Specifically, while the separation phase stabilizer for the crude product, or the isolated liquid product, resulting from the one-step or two-step process may be the same as the reaction phase stabilizer, the separation phase stabilizer to be added to each fraction or mass of material collected from the separation process will typically be different, frost especially in the case of the finally purified material. Following on the foregoing, it is also to be appreciated that a given process may involve different separation phase stabilizers during the full course of the separation, purification and recovery steps. For example, while one separation phase stabilizer system may be employed for each distillation step or a multi-step distillation, a different separation phase stabilizer may be used in the final, purified products (and hence its collection vessel if pre-treated).

The improved separation process of the present invention may be applied to any of the known processes for the fractionation or separation, purification and recovery of methylidene malonates. Such methodologies include: distillation (including fractional distillation), flash distillation, solvent stripping, crystallization, precipitation, extraction, gel filtration, electrophoresis, foam fractionation, electromagnetic separation, evaporation (including thin film evaporation), press extraction, and various forms of chromatography as well as combinations of the foregoing. For convenience, the following discussion will be made with respect to distillation, notably fractional distillation; though it is to be appreciated that those skilled in the art will readily appreciate the modifications and variations that will be needed to adopt the process to the other fractionation methods.

Furthermore, as noted above, the improved separation process may be applied to the stabilized crude reaction product or crude liquid reaction product of the improved reaction process described above. From a commercial perspective, it is preferred that it be adopted as a continuation of that process; although, it can also be applied to those products following storage of the same. More importantly, it is to be appreciated that this improved separation process is also applicable to the fractionation of crude products and crude liquid products resulting from other known methods for the production of methylidene malonates. For example, it may be applied to those unstabilized or alternatively stabilized crude methylidene malonate products resulting from any of the adduct-free methods known in the art, including, for example, Bachman (U.S. Pat. No. 2,313,501), D'Alelio (U.S. Pat. No. 2,330,033), Coover et. al. (U.S. Pat. No. 3,221,745 and U.S. Pat. No. 3,523,097) and in Freely et. al., Organic Syntheses, Coll. Vol. 4, p. 298 (1963); Vol. 38, p. 22 (1958), which are all hereby incorporated herein by reference. It may also be applied to those stabilized crude methylidene malonate reaction products resulting from the improved solvent free adduct methods disclosed in U.S. Provisional Patent Application Ser. No. 61/215,578, filed May 7, 2009, and U.S. patent application Ser. No. 12/774,817, now U.S. Pat. No. 8,106,234 B2, which claims the benefit of said provisional application, both of which are incorporated herein by reference as well as those crude products produced in the known adduct processes including Hawkins et. al. (U.S. Pat. No. 4,049,698), Ponticello (U.S. Pat. No. 4,056,543), Ponticello et. al. (U.S. Pat. No. 4,160,864), and Bru-Magniez et. al. (U.S. Pat. No. 4,932,584 and U.S. Pat. No. 5,142,098), all of which are hereby incorporated herein in their entirety by reference.

Where the crude product, whether formed by an adduct process or an adduct-free process, to be subjected to the improved separation process of the present invention is not stabilized, then one should first add a separation phase stabilizer system to the crude products before commencing fractionation. This separation phase stabilizer system may be the same or different from the separation phase stabilizer system to be added to the recovered fractions. Similarly, even if the crude product to be subjected to fractionation contained an alternate stabilizer or stabilizer system, one may consider supplementing, and preferably will supplement, the stabilization of the crude product with an amount of the separation phase stabilizer system.

While the separation phase stabilizer system may be added to the recovered material during or following its collection, it is preferred that at least a portion of the separation phase stabilizer system be added to the collection flask or vessel prior to initiating fractionation or at least prior to collection of the fraction to be recovered and the remainder added following completion of the fractionation or, as appropriate, collection of the given fraction(s). The amount of the separation phase stabilizer system to be added to the empty collection flask or vessel will be based on the projected amount of material to be collected: generally the amount will be somewhat less than that needed if the full amount projected were to actually be recovered. Once the fractionation is completed, the level of separation phase stabilizer will then be adjusted upward, as appropriate, based on the actual amount collected. And, as with the reaction phase stabilizer system, it is preferred, though not required, that all components of the separation phase stabilizer system be added concurrently or nearly so. The exception, of course, is where a vapor phase stabilizer is to be continuously introduced to the fractionation apparatus, as further described below.

The process as described above, i.e., the addition of the separation phase stabilizer system, will be used for each successive fractionation process and/or fractionation step employed. For example, in fractional distillation, if a given fraction or combination of fractions is to be redistilled, the fractions collected during the redistillation will also be stabilized with the separation phase stabilizer and the materials to be fractionated will be up-stabilized, as appropriate.

In the practice of the preferred embodiment of this aspect of the present invention, it is most convenient to place a quantity of a stock solution of the separation phase stabilizer system, or one or more components thereof, especially, the anionic polymerization, in the collection vessel or container, allow the solution to evenly coat the inner surface of the collection vessel or container and then pour out the excess. Since the solvent for the stock solution is typically a volatile solvent, e.g., toluene, ethanol, acetone, etc., or a copolymerizable or an inert monomer, e.g., an acetate or acrylate, the container or vessel is promptly attached to the fractionation apparatus or sealed to prevent loss of the stabilizer solution until the container or vessel is to be attached to the fractionation apparatus. On the other hand, so long as the loss of solvent will not affect the inhibitors in the vessel, which essentially coat the inside wall of the vessel, one may allow some or all of the solvent to evaporate before sealing to protect the remaining inhibitors. One can calculate the amount of inhibitor(s) left in the container or vessel by weighing the weight gain. Then, once the separation process is completed and the collected sample sealed in the container, the container is then again weighed and the proper weight of the recovered material determined so that one can then determine the amount of stabilizer to be added to bring the total stabilizer content to the appropriate level.

Depending upon the nature of the fractionation process employed, it is preferred to include one or more vapor, phase or dual liquid-vapor phase anionic polymerization inhibitors in the separation phase stabilizer system. This is particularly so for those fractionation processes which involve the formation of a vapor of or containing the methylidene malonate. If the system is a closed or sealed system, then one only need add the vapor phase stabilizer with the liquid phase stabilizer. However, if it is an open system or a system under a drawn vacuum, then it is necessary to supply a continuous feed of the vapor phase stabilizer to maintain a given level of the stabilizer in the vapor phase or the airspace of the apparatus. For example, in a traditional distillation apparatus, especially one that is under vacuum, it is preferred to bubble a constant vapor of the vapor or dual liquid-vapor phase polymerization inhibitor through the system.

The adoption of either or both of the improved reaction and separation processes described above results in a marked stability to the overall process, thereby enabling consistent and more predictable results. In addition to the enhanced stability and, hence, predictability achieved by the use of the stabilizer systems, their use also results in still higher yields of greater purity, particularly as compared to the performance of similar processes conducted in the absence of polymerization inhibitors or with other stabilizers.

Specifically, by implementing the improved processes as set forth herein, one realizes more consistent and improved yields. For example, one may attain crude yields in excess of 35%, preferably in excess of 45%, more preferably in excess of 60%. In those situations where the improved separation process of the present invention is applied to non-adduct processes, as mentioned above, one may attain yields in excess of 25%, preferably in excess of 35%, more preferably in excess of 40%, most preferably in excess of 50% or more, on a consistent and repeatable basis. This is surprising in light of the prior art teachings as set forth in the Background. Regardless, of particular importance is the fact that these yields are attained with a concomitant high purity, generally 60% or more, preferably 75% or more, more preferably 80% or more, most preferably 90% or more, with or without the use of the intermediate adducts. More importantly, the further fractionation of these yields by the improved separation process and associated separation phase stabilizer system results in even higher purities with excellent yields. Generally, one is able to realize purified yields in excess of 20%, preferably in excess of 30%, more preferably in excess of 35%, most preferably of about 40% or more, based on the original malonate reactant, on a repeatable and consistent basis. Furthermore, these "purified" fractions or collections of methylidene malonate generally have purities exceeding 80%, preferably 85%, more preferably 90%, most preferably 95%. Thus, even if the yields, especially the purified yields, slip below the aforementioned targets, the loss in yield is more than made up for by the increased purity attained with the improved processes. Hence; yields as low as 15%, even 10%, with high purity of 85% or higher, preferably 90% or higher, most preferably 95% or higher, provides a suitable process and is within the scope of the present invention. Generally speaking, the improved processes of the present invention provide for high purity wherein the purified product contains less than 8%, preferably less than 6%, most preferably less than 4%, of impurities and less than 12%, preferably less than 10%, most preferably less than 8% of the analogs of the desired product, on a consistent basis.

Thus, while there may be, and most likely is, some loss in overall yield as a result of the fractionation process, especially if multiple fractionation processes are employed or the same process is repeated one or more times, the purity of the product significantly improves. This is especially important from a commercial perspective as the purity of the methylidene malonate is critical to and correlates with its utility and performance. Specifically, as discussed in Coover et. al. (U.S. Pat. No. 3,221,745) and as found by Applicants, even minor amounts of impurities impair their utility, especially the cure or polymerization characteristics of these monomers. Concern with the presence and amount of impurities and byproducts is even more paramount, if not an absolute use limiting factor, in the case of methylidene malonates intended for medical applications, especially skin bonding applications, e.g., skin bonding adhesives, or other applications that may require its use in the human body.

Having generally described the use and application of the stabilizer systems and the improved processes employing the same, attention now is drawn to the two stabilizer systems and their respective constituents.

According to the present invention, suitable anionic polymerization inhibitors are characterized as being strong acids, most preferably very strong acids. As used herein, a strong acid is an acid that has an aqueous pKa of about 2.0 or less and a very strong acid is one having an aqueous pKa of 1.0 or less. Strong acids include, but are not limited to strong mineral acids and strong organic acids including maleic acid, difluoroacetic acid, dichloroacetic acid, and picric acid. The very strong acids include, but are not limited to the very strong mineral and/or oxygenated acids as well as the sulfonic acids. By way of example, but not limitation, exemplary very strong acids include sulfuric acid, nitric acid, perchloric acid, trifluoroacetic acid, trichloroacetic acid, hydrochloric acid, hydrobromic acid, benzene sulfonic acid, methane sulfonic acid, trifluoromethane sulfonic acid, fluorosulfonic acid, chlorosulfonic acid, paratoluene sulfonic acid, and the like. Preferably the anionic polymerization inhibitor is selected from trifluoroacetic acid, sulfuric acid, perchloric acid or chlorosulfonic acid, most preferably sulfuric acid and/or trifluoroacetic acid. The latter has the added benefit of serving as both a liquid and vapor phase inhibitor since a sufficient amount distills over with the monomer: thereby stabilizing the vapor phase as well.

Since the present invention is not limited to aqueous systems, it is to be noted that not all acids dissociate to the same degree in different medium. Hence, it is to be understood that, especially in the context of non-aqueous based systems and media, the strong acids and very strong acids must exhibit sufficient dissociation to manifest a sufficient degree of the acid effect on polymerization inhibition. The degree of dissociation may be determined empirically by measuring the conductivity of the medium to which the acid is added: a higher conductivity being evidence of a greater degree of dissociation. Additionally, with certain exceptions, it is preferred that the chosen polymerization inhibitors, whether for aqueous or non-aqueous systems, are such that they will not readily distill over during the distillation process of the crude material or the subsequent distillations. Rather, it is generally preferred that no or negligible amounts of the polymerization inhibitors distill over. The exception, however, are those polymerization inhibitors that distill over slowly so as to remain in sufficient quantities in the distillation vessel to prevent premature polymerization prior to completion or substantial completion of the distillation process and which also serve as a polymerization inhibitor of the vapor phase as it traverses to the collection flask.

Generally speaking the amount of anionic polymerization inhibitor to be added to the system should be from about 1 to about 10,000 ppm, preferably from about 5 to about 6000 ppm, most preferably from about 100 to about 5000 ppm, based on the amount of malonic acid ester or, as appropriate, the adduct thereof. For certain processes and conditions, as noted in the examples, the amount of anionic polymerization inhibitor was preferably from about 1000 to about 4000, most preferably from about 2500 to about 3500 ppm based on the amount of malonic acid ester or, as appropriate, the adduct thereof. Generally, the amount of anionic polymerization inhibitor to use can be determined by simple experimentation.

Also, as mentioned, the improved processes of the present invention may include, and preferably does include, one or more free radical polymerization inhibitors. Suitable free radical inhibitors include, but are not limited to, the quinones and hindered phenols, especially the hydroquinones, hydroquinones monomethyl ether, catechol, pyrogallol, benzoquinones, 2-hydroxy benzoquinones, p-methoxy phenol, t-butyl catechol, butylated hydroxy anisole (BHA), butylated hydroxy toluene (BHT), t-butyl hydroquinones, 2,2"-methylene-bis(6-tertbutyl-4-methylephenol), and mixtures thereof. Generally speaking the amount of free radical inhibitor to be added to the system should be from about 100 to about 20,000, preferably from about 300 to about 10,000, most preferably from about 2000 to about 5000 ppm based on the amount of malonic acid ester or, as appropriate, the adduct thereof. Generally, the amount of free radical polymerization inhibitor to use can be determined by simple experimentation.

In preferred embodiments, a combination of at least one anionic polymerization inhibitor and at least one free radical polymerization inhibitor will be employed. The inhibitor system may be added as a single mixture of all inhibitors or each inhibitor may be added separately.

It is also contemplated that one or more secondary anionic active agents may be used in combination with the required polymerization inhibitors. Such secondary anionic active agents include vapor phase anionic polymerization inhibitors such as sulfur dioxide, boron trifluoride, or hydrogen fluoride, or combinations of any two or all three as well as liquid phase anionic polymerization inhibitors that do not meet the aforementioned requirements of a suitable strong acid. Such secondary liquid phase anionic inhibitors include those acids having an aqueous pKa of more than 2 and/or having low conductivity in the non-aqueous medium. Exemplary secondary liquid phase anionic inhibitors include, but are not limited to phosphoric acid; organic acids such as acetic acid, benzoic acid, chloroacetic acid, cyanoacetic acid and mixtures thereof, especially acetic acid, benzoic acid or mixtures thereof.

The amount of the secondary anionic active agent will vary depending upon the strength of the same in inhibiting anionic polymerization and the nature of the polymerization inhibitor used. For example, vapor phase polymerization inhibitors will generally be employed at a level of from 1 to about 200 ppm, preferably from about 10 to about 100 ppm. The liquid phase secondary polymerization inhibitors will generally be present at a level of from about 5 to about 500 ppm, preferably from about 25 to about 400 ppm for the weaker acids such as acetic or benzoic acid whereas lesser amounts, such as from about 20 to about 200 ppm, preferably from about 40 to about 100 ppm will suffice for the stronger acids such as phosphoric acid. While it is to be appreciated that the amount of such secondary inhibitors is not to be included when calculating the weight percent of aforementioned primary anionic polymerization inhibitors, their presence oftentimes enables one to use less of the latter to achieve the same level of stability in the improved methylidene malonate process of the present invention.

Thus, in its broadest concept, the present invention relates to an improvement in those processes for the production of methylidene malonates wherein the latter are stripped from an adduct or like intermediate based on a conjugated diene or polynuclear aromatic platform wherein the improvement is the inclusion of the aforementioned polymerization inhibitors, preferably a combination of the anionic and free radical polymerization inhibitors, in the reaction medium during the stripping step. Most commonly, such stripping is achieved by pyrolysis or thermolysis or by heat treatment at lower temperatures in the presence of a compound, also referred to as a stripping agent, that directly or indirectly facilitates the stripping of the methylidene malonate from the adduct. It is believed, though not confirmed, that the stripping agent, under the elevated temperature conditions, actually substitutes for the methylidene malonate on the conjugated diene or polynuclear aromatic platform. As mentioned, these polymerization inhibitors will also preferably be present in the resultant mix during the subsequent distillation step(s). Furthermore, it is also possible that some of these polymerization inhibitors may be present in the initial, if not subsequent, distillates, lending stabilization to the isolated, purified methylidene malonate. In those processes where the medium containing the stripped material is first subjected to a separation step before distillation, it is desirable and preferable to add additional polymerization inhibitors to that phase containing the methylidene malonate to prevent polymerization during the subsequent distillation or in bulk storage of the unpurified materials.

Having generally described the use and application of the stabilizer systems and the improved processes employing the same, attention now is drawn to the two stabilizer systems and their respective constituents.

The reaction phase stabilizer system comprises at least one anionic polymerization inhibitor (also referred to as the primary anionic polymerization inhibitor), at least one of which is a liquid phase anionic polymerization inhibitor, alone or in combination with at least one inhibitor of free radical polymerization. Preferably the primary anionic polymerization inhibitor(s) is an acid, especially a mineral acid, an organic acid, or a sulfonic acid. Especially suitable anionic polymerization inhibitors are characterized as being strong acids, most preferably very strong acids. As used herein, a strong acid is an acid that has an aqueous pKa at room temperature of about 2.0 or less and a very strong acid is one having an aqueous pKa of about 1.0 or less. Strong acids include, but are not limited to, strong mineral acids and strong organic acids including maleic acid, difluoroacetic acid, dichloroacetic acid, and picric acid. The very strong acids include, but are not limited to, the very strong mineral and/or oxygenated acids as well as the sulfonic acids. By way of example, but not limitation, exemplary very strong acids include sulfuric acid, nitric acid, perchloric acid, trifluoroacetic acid, trichloroacetic acid, hydrochloric acid, hydrobromic acid, benzene sulfonic acid, methane sulfonic acid, trifluoromethane sulfonic acid, fluorosulfonic acid, chlorosulfonic acid, paratoluene sulfonic acid, and the like. Preferably the primary anionic polymerization inhibitor is selected from trifluoroacetic acid, sulfuric acid, maleic acid, perchloric acid and chlorosulfonic acid; most preferably sulfuric acid, maleic acid, and/or trifluoroacetic acid. In part, the selection of the stabilizer is temperature dependent. For example, high temperature adduct processes favored the use of maleic acid as the reaction phase stabilizer over sulfuric acid. The latter, though, appears to be preferred over the maleic acid when adding it to the isolated product.

With certain exceptions, it is preferred that the individual polymerization inhibitors making up the reaction phase stabilizer system are not readily vaporized or otherwise drawn or removed from the crude product or crude liquid product, as appropriate, on standing or under the selected fractionation technique to be employed for the separation and recovery of the purified methylidene malonate. This is especially important in high temperature separation steps such as distillation, particularly fractional distillation. While the passing over of small amounts of the anionic polymerization inhibitor may be tolerated and acceptable, it is generally preferred that no or negligible amounts pass over so as to avoid the happenstance that the crude reaction product becomes deficient in the amount of stabilizer present before separation is completed. A deficiency in the level of the stabilizers will lead to a general instability of the reaction product which, in turn can lead to an undesirable and untimely formation of oligomers and/or polymers of the methylidene malonate and/or the formation of other byproducts and degradation products, especially glutarates: all of which will reduce significantly the yield of recovered material in the collection vessel.

The first exception is where the anionic stabilizer is employed in a sufficient excess to account for the loss or passing over of the stabilizer in the vapor phase.

The second exception to the foregoing is polymerization inhibitors that distill over slowly so as to remain in sufficient quantities in the crude reaction product or crude liquid reaction product so as to prevent its premature polymerization prior to completion or substantial completion of the separation process. These inhibitors have the added benefit of serving as a stabilizer of the vapor phase as it traverses to the collection flask. Thus, for the purpose of this application and the appended claims, dual functional liquid-vapor phase anionic polymerization inhibitors are to be deemed liquid phase anionic polymerization inhibitors: thereby satisfying the need for the at least one liquid phase anionic polymerization inhibitor. An example of an anionic polymerization inhibitor capable of acting as both a liquid phase and vapor phase stabilizer is trifluoroacetic acid. When such dual functional anionic polymerization inhibitors are used, it may be desirable to add a bit more of the inhibitor to the reaction vessel so as to account for the loss during the separation step.

Another exception is where the reaction phase stabilizer system further comprises a secondary anionic polymerization inhibitor that is or has the capacity to act as a vapor phase polymerization inhibitor or as a dual vapor-liquid phase polymerization inhibitor. As discussed in greater detail below, such secondary vapor phase and dual liquid-vapor phase anionic polymerization inhibitors include sulfur dioxide ($SO_2$), boron trifluoride ($BF_3$), nitric oxide (NO) or hydrogen fluoride (HF).

Generally speaking, the amount of the primary anionic polymerization inhibitor to be employed during the reaction phase should be from about 1 ppm to about 10,000 ppm, preferably from about 5 ppm to about 6,000 ppm, more preferably from about 100 to about 5,000 ppm. Of course, the specific amount will vary depending upon the strength of the anionic polymerization inhibitor: in the case of an acid, the pKa value. Generally, it appears that the stronger the polymerization inhibitor, the lesser the quantity of anionic polymerization inhibitor needed. For example, a strongly acidic anionic polymerization inhibitor like sulfuric acid may be used in quantities in the lower end of the range, e.g., from about 1 to about 2000, preferably from about 5 to about 500, more preferably from about 10 to about 200 ppm, most preferably from about 10 to about 100 ppm. On the other hand, a comparatively weaker acid, like maleic acid, will be used towards the higher end of the range, generally from about 100 to about 5000, preferably from about 500 to about 4500, more preferably from about 1000 to about 4000, most preferably from about 2500 to about 3500 ppm based on the amount of the malonic acid ester or precursor thereof. Generally, the amount of anionic polymerization inhibitor to use can be determined by simple experimentation.

As indicated above, the reaction phase stabilizer system may also comprise, as an option, one or more secondary anionic polymerization inhibitors. These are generally anionic polymerization inhibitors that, on their own, do not appear to perform well as the sole or primary reaction phase anionic polymerization inhibitor, but which, when combined with the latter, provide an additive or synergistic stabilization effect to the overall crude product and reaction system. Suitable secondary anionic polymerization inhibitors include liquid phase, vapor phase, and dual liquid-vapor phase anionic polymerization inhibitors. Generally, secondary anionic polymerization inhibitors are also acids, especially, but not exclusively, those having an aqueous pKa of more than 2, more commonly more than 3, and/or having low conductivity in the non-aqueous medium. Exemplary secondary anionic polymerization inhibitors include, but are not limited to phosphoric acid; phosphorus pentoxide ($P_2O_5$); organic acids such as acetic acid, benzoic acid, fumaric acid, chloroacetic acid, cyanoacetic acid and mixtures thereof, especially acetic acid, benzoic acid or mixtures thereof; sulfur dioxide; nitric oxide; boron trifluoride; and hydrogen fluoride; as well as combinations of any two or more of the foregoing. As mentioned above, certain of these secondary anionic polymerization inhibitors, including sulfur dioxide, nitric oxide, boron trifluoride, and hydrogen fluoride, are or are also capable of acting as vapor phase anionic polymerization inhibitors. Additional exemplary secondary anionic polymerization inhibitors, including vapor phase inhibitors, and mixtures thereof are set forth in Malofsky et. al., U.S. Pat. No. 6,512,023 B1, which is hereby incorporated herein in its entirety by reference.

The amount of the secondary anionic polymerization inhibitor to be employed, if present, will vary depending upon the strength of the same in inhibiting anionic polymerization and the nature of the stabilizer used. For example, the secondary anionic polymerization inhibitors will generally be employed at a level of from about 1 to about 500 ppm, preferably from about 10 to about 400 ppm, most preferably from about 15 to about 200 ppm. As with the primary anionic polymerization inhibitors discussed above, the strength of the inhibitor will also affect its level of use. For example, for the weaker acids such as acetic or benzoic acid, 25 to 400 ppm may be more appropriate whereas lesser amounts, such as from about 5 to about 200 ppm, preferably from about 15 to about 100 ppm will suffice for the stronger acids such as phosphoric acid. Similarly, when a vapor phase secondary anionic polymerization inhibitor is present, it will generally be employed at a level of from 1 to about 500 ppm, preferably from about 5 to about 200 ppm, more preferably from about 10 to about 100 ppm. For purposes of clarification, the amount of the secondary anionic polymerization inhibitor, when present, is in addition to the amount of the primary anionic polymerization inhibitor mentioned above.

As mentioned above, the reaction phase stabilizer system employed in the improved processes of the present invention may also include, and preferably does include, one or more free radical polymerization inhibitors. Suitable free radical inhibitors include, but are not limited to, the quinones and hindered phenols, especially the hydroquinones, hydroquinone monomethyl ether, catechol, pyrogallol, benzoquinones, 2-hydroxy benzoquinones, p-methoxy phenol, t-butyl catechol, butylated hydroxy anisole (BHA), butylated hydroxy toluene (BHT), t-butyl hydroquinones, 2,2"-methylene-bis(6-tertbutyl-4-methylephenol), and mixtures thereof. Generally speaking the amount of free radical inhibitor to be added to the system should be from about 100 to about 20,000, preferably from about 300 to about 10,000, more preferably from about 500 to about 5000 ppm, most preferably from about 800 to about 2000 ppm, based on the amount of malonic acid ester or, as appropriate, the adduct thereof. Generally, the optimal amount of free radical polymerization inhibitor to use for the particular system can be determined by simple experimentation.

Of course, a number of process variables may affect the amount and selection of the specific inhibitors to be employed in the reaction phase stabilizer system and are to be considered when formulating the stabilizer system. Process variables such as the reaction medium, the temperature at which the reaction is run, the reactants, the intended products, as well as the byproducts typically formed, can all affect the performance and selection of the various stabilizer(s) making up the reaction phase stabilizer system. For example, reaction processes employing or encountering higher temperatures seem to favor the stronger acids, like sulfuric acid; whereas, lower temperature processes seem to favor the comparatively weaker acids, like maleic acid.

Perhaps one of the most important variables affecting performance is the degree of dissociation of the selected polymerization inhibitors in the reaction medium, especially non-aqueous based reaction media. In this respect, it is particularly important, if not paramount, that sufficient dissociation of the inhibitors, especially the primary anionic polymerization inhibitors, take place to manifest a sufficient degree of the acid effect on polymerization inhibition. As discussed in Malofsky et. al. (U.S. Pat. No. 6,512,023), one may determine the degree of dissociation empirically by measuring the conductivity of the medium into which the acid is added in order to assess sufficient dissociation: a higher conductivity being evidence of a greater degree of dissociation.

Where the degree of dissociation in a particular medium or reaction mix is of concern, one may enhance dissociation or overcome this issue by forming stock solutions of one or more of the selected polymerization inhibitors wherein the inhibitors are first dissociated or dissolved in a favorable media or solvent before being added to the reaction mix or crude reaction product. Those skilled in the art will readily recognize suitable media and solvents for a given inhibitor or inhibitor combination as well as compatible media or solvents for the given reaction media or reactant mix. This can also be determined by simple experimentation. Exemplary media or solvents for forming such stock solutions are cyanoacetic acid, toluene and a combination thereof As discussed above, the present invention also provides for an improved process for the separation, purification and recovery, i.e., fractionation, of methylidene malonate wherein the improvement comprises the use of a second stabilizer system, the separation phase stabilizer system, during the fractionation process(es). The separation phase stabilizer system comprises one or more primary anionic polymerization inhibitors, one or more secondary polymerization inhibitors, or a combination of the two, alone or in further combination with one or more free radical polymerization inhibitors, all as described above with respect to the components of the reaction phase stabilizer system. Indeed, while not necessary, it is to be appreciated that the separation phase stabilizer system may be the very same stabilizer system as the reaction phase stabilizer system. Similarly, except as noted below with respect to a vapor or dual liquid-vapor phase stabilizer, the amounts by which the individual polymerization inhibitors of the separation phase polymerization inhibitors are used is also consistent with that of the reaction phase stabilizer systems; though the tendency may be that their use is towards the middle and lower end of the ranges specified above so as not to subsequently affect the cure or polymerization characteristics of the purified monomer. Here, however, it is to be remembered that the amount is based upon the amount of methylidene malonate product expected and/or actually recovered from the separation process, not the malonate precursor material. Additionally, where the sole anionic polymerization inhibitor of the separation phase stabilizer system is a secondary anionic polymerization inhibitor, the amount to be employed will be consistent with the amount which would have been used if it were a primary anionic polymerization inhibitor as opposed to the lesser amounts used when a secondary anionic polymerization inhibitor is used to supplement the primary anionic polymerization inhibitor as set forth above.

When used, the amount of vapor phase or dual liquid-vapor phase anionic polymerization inhibitor to be employed in the improved fractionation process will vary depending upon the nature of the fractionation process itself. If the fractionation process is conducted in a closed system, one where there is no flow of air or other gas in or through the fractionation apparatus, or the collected volume is to be stored, whether as monomer or formulated material, then the vapor phase inhibitor will generally be employed at a level of from 1 to about 500 ppm, preferably from about 5 to about 200 ppm, more preferably from about 10 to about 100 ppm. However, where the fractionation process is conducted in an open system or under vacuum, one must account for the loss of the vapor phase stabilizer. Hence, in those processes, it is preferred to continuously introduce vapor phase stabilizer to the given system or apparatus, e.g., by bubbling, in order to maintain a concentration consistent with the levels mentioned for the closes systems. As note above, suitable vapor phase and dual liquid-vapor phase stabilizers include, trifluoroacetic acid, sulfur dioxide, boron trifluoride and hydrogen fluoride. Of course, the vapor phase stabilizer may be added to the liquid component as well as bubbled in, especially where the stabilizer is a dual liquid-vapor phase stabilizer.

As known in the art, the methylidene malonates formed by the improved process of the present invention may be employed in a number of organic syntheses and polymer chemistry applications. In particular, they are especially useful in the preparation of various adhesive and sealant applications including industrial, commercial and consumer adhesive and sealant applications as well as in skin bonding applications for human and animal skin bonding. In light of the benefit of the present invention, it is believed that these compositions are now commercially viable as cost effective and stable formulations can now be made.

Having described the invention in general terms, Applicants now turn to the following examples in which specific combinations of reactants, solvents and stabilizers as well as varied reaction times were evaluated. These examples are presented as demonstrating the surprising attributes of the improved processes of the present invention as well as the unexpected synergy resulting from the use of the combination of the anionic and free radical polymerization inhibitors. These examples are merely illustrative of the invention and are not to be deemed limiting thereof. Those skilled in the art will recognize many variations that are within the spirit of the invention and scope of the claims.

EXAMPLES

Having described the invention in general terms, Applicants now turn to the following examples in which specific combinations of reactants, solvents and polymerization inhibitors as well as varied reaction times were evaluated. These examples are presented as demonstrating the surprising attributes of the improved processes of the present invention as well as the unexpected synergy resulting from the use of the combination of the anionic and free radical polymerization inhibitors. These examples are merely illustrative of the invention and are not to be deemed limiting thereof. Those skilled in the art will recognize many variations that are within the spirit of the invention and scope of the claims.

In conducting the experiments, preformed malonate adducts obtained from Virsol of Paris, France were employed. To recover the desired methylidene malonate from the malonate adduct, the following general stripping (reverse Diels-Alder) and distillation procedures were followed. It is to be noted that while crude distillation, as discussed below, is the preferred method for the initial recovery of the crude product from the reaction mix or mash, other methods such as filtration, with or without, distillation, may also be employed.

Reverse Diels-Alder: The listed reactants—adduct, maleic anhydride, solvent (paraffin oil ("PO") or tricresyl phosphate ("TCP")), and free radical inhibitor (hydroquinone ("HQ"))—were charged to the reactor. The condenser water was then turned on and the contents mixed thoroughly until the mixture appeared homogeneous. Thereafter, the anionic polymerization inhibitor (concentrated sulfuric acid ("$H_2SO_4$")) was added with continual mixing until intimately dispersed in the matrix. The reactants were then gradually heated to the proper reflux or desired reaction temperature and held at that temperature for a sufficient period of time to effectuate and ensure a complete, or nearly so, reverse Diels-Alder reaction.

Distillation: Typically, a two-step distillation process is employed, the first results in the recovery of crude product and the second the recovery of a purified distillate.

Crude Product: With the heat off, the product of the reverse Diels-Alder reaction is allowed to cool to <80° C. and the system is then subjected to a vacuum. The vacuum is applied slowly to control foaming of the reactor contents until a pressure in the range of 0.1 to 0.4 mm Hg is attained. Once the proper vacuum is attained, heat is applied to the contents of the reactor to initiate the crude distillation, e.g., by immersion of the reactor vessel in a hot oil bath, ~225° C. Because maleic anhydride remains in the crude product following the reaction and has a lower boiling point than the methylidene malonates, the first cut of the crude distillation is almost exclusively maleic anhydride. To prevent its condensation, including crystallization, in the distillation apparatus, it is preferred to heat the distillation pathway to ensure that the maleic anhydride will not condense until the collection vessel. Once material stops condensing over and the temperature of the system rises, the collection vessel containing the maleic anhydride is removed and replaced with a clean, pre-stabilized vessel. Thereafter, heating is resumed and continued until the distillation is completed: this may be signified by, among other signs, the appearance of a whitish substance in the flow path. The actual crude distillation and head temperatures as well as the timing of the crude distillation will vary depending upon the specific methylidene malonate being isolated and the other components of the reaction mix. Thereafter, the heat is shut off and the remaining reactor mixture is allowed to cool while the system is maintained under vacuum. Once the reactor temperature reaches 100° C., the system is allowed to equilibrate to atmospheric pressure by bleeding air into the system, e.g., through the vacuum takeoff, preferably through a drierite (anhydrous calcium sulfate) tube or a similar suitable anhydrous material containing tube. The crude product in the collection flask is then redistilled or stored for subsequent redistillation or, if the collection flask also includes a substantial quantity of the solvent, as is the case of the process in which paraffin oil is employed, subjected to a separation process to remove all or substantially all of the paraffin oil. In any event, where the crude product is to be stored, it is preferably stabilized with additional polymerization inhibitors and stored under refrigerated conditions, typically from 2° to 8° C.

Redistillation: With no heat, the crude product (also referred to as the crude yield) is slowly subjected to a vacuum. During this step, any solvent, e.g., n-heptane, used in the extraction/separation step, if any, will come over and collect. When a vacuum of less than 0.5 mm Hg is attained, dry air is bled through the system and the vacuum trap emptied of any materials collected. Heat is then applied to the reactor contents at a moderate rate to initiate the initial redistillation. This distillation is allowed to continue until completed: completion may be signified by a drop in temperature and/or pressure.

Separation: Depending upon the medium in which the stripping is conducted, it may be desirable or necessary to conduct one or more separations in order to maximize the recovery of the methylidene malonate and/or to remove excess medium and other remaining reactants from the adduct forming process. For example, when using paraffin oil as the medium for the stripping reaction, the resultant product produces two layers, an upper layer comprising a paraffin oil/crude monomer emulsion and a lower layer comprising crude monomer. The upper layer is to be removed and washed with an alkane, e.g., n-heptane, n-pentane, etc., to extract the crude monomer. This extraction process may be repeated as necessary.

Of course, separation may also be employed advantageously as an intermediate step between the first and second steps of the two-step process. Here the reaction mix may be washed with suitable solvents, e.g., diethyl ether, or dissolved in chloroform and washed with, e.g., saturated ammonium chloride and/or saturated sodium chloride solutions, depending upon the particular reactants and reaction processes followed: all as is known in the art.

Stabilization: In order to ensure good stability of the collected methylidene malonate during the crude distillation, it is desirable to add additional polymerization inhibitors to the crude product and the collection flask. Similarly, in the redistillation process(es), additional polymerization inhibitors are preferably added to the collection flask prior to commencing the distillation with the amount added based on the expected yield. The polymerization inhibitors added to the collection flasks may be the same as are added to the reaction mix during the stripping process or they may be other inhibitors known or found suitable for stabilizing the distilled monomer materials, especially those that would be suitable for use in the final products formulations such as trifluoroacetic acid (TFA) or a combination of $SO_2$ and sulfuric acid. The former has the added benefit of being relatively non-reactive towards the degradation products of the monomer as compared to the latter combination. This is particularly beneficial for long term stability. Generally speaking the amount of polymerization inhibitor in the collection flasks should be approximately 10 ppm anionic polymerization inhibitor and 100 ppm free radical inhibitor based on the anticipated yield of monomer: though higher and lower levels can be used depending upon the particular formulation as well known in the art or as can easily be determined by simple experimentation. Should it be found that the amount initially added to the flask was low, additional polymerization inhibitors should be added to raise the level up to enhance stability.

In performing the stripping and distillation processes, an apparatus comprising a resin kettle reactor vessel equipped with a distillation head—claisen adapter/temperature well/condenser, vacuum takeoff adapter and a 4-way cow receiver with adequately sized collection flasks and vacuum port was employed.

Examples E1-E11, Comparative Examples CE1-CE5

A series of reactions, with and without polymerization inhibitors, were performed to strip and recover 1-ethoxycarbonyl-1-ethoxycarbonyl methylene oxycarbonyl ethane (formula I wherein $R^1=$—$CH_2CH_3$ and $R^2=$—$CH_2CO_2CH_2CH_3$) from the 2.1.2 adduct (11-ethoxycarbonyl-11-ethoxycarbonyl methylene oxycarbonyl-9,10-endoethano-9,10-dihydroanthracene). The identity and quantity of reactants and solvent medium (paraffin oil (PO)) added to the reactor vessel for conducting the stripping reaction were as set forth in Table 1. Table 1 also identifies the various levels at which the anionic polymerization inhibitor (sulfuric acid) and the free radical polymerization inhibitor (hydroquinones (HQ)) were added. The former was typically added after the other components had been well mixed. Thereafter, the reactor was heated to 185° C. and the temperature held, and the reactor contents allowed to react for the period specified in Table 1.

Following reaction, the heat was removed and the contents of the reactor allowed to cool to <80° C. With the heat off, a vacuum was slowly applied to the system: slow enough to control foaming of the reactor contents. Once a vacuum of 0.1 to 0.4 mm Hg was attained with no further foaming, the reactor contents were heated to initiate distillation. Distillation continued to a reactor temperature of about 170° C. and a head temperature in the range of 140-150° C. Once distillation is completed, e.g., the formation of a whitish substance at the temperature well of the distillation head/claisen adapter oftentimes signified the later stage of the recoverable distillate, heating was discontinued and the contents of the reactor allowed to cool while maintaining vacuum. Once the temperature reached 100° C., the system was equilibrated to atmospheric pressure and the contents transferred to a separatory funnel. The collection flask was then washed with 800 g n-heptane and the contents added to the separatory funnel. The latter was then shaken well and the layers allowed to separate. The lower phase containing the crude methylidene malonate product was decanted into the collection flask and the upper phase, the n-heptane wash, placed in another vessel. The process was then repeated with fresh n-heptane. The n-heptane washes were allowed to separate overnight and the lower phase added to the crude product. The crude product was then stabilized to 10 ppm concentrated sulfuric acid and 100 ppm hydroquinone and stored under refrigerated conditions (2°-8° C.) until redistillation.

Redistillation was effected in the same apparatus as the initial distillation: again the collection flask is prestabilized with sufficient sulfuric acid and hydroquinone to achieve a level of 10 ppm of the former and 100 ppm of the latter based on the anticipated yield. Once again a vacuum was applied slowly to control foaming of the crude product, essentially trapped air and residual n-heptane. A significant amount of n-heptane is found to be collected in the vacuum trap. Once a vacuum of less than 0.5 mm Hg is achieved, dry air is bled through the system and the trap emptied. The reactor vessel is then heated at a moderate rate to begin distillation. Distilled product will begin to collect at a reactor temperature of 75-80° C. and a head temperature of ~30° C. Distillation is continued, collecting four evenly weighted fractions, to a reactor temperature of 215° C. and a head temperature of ~96-98° C. Distillation is completed when the reactor temperature drops from 215° C. to 205° C. and the head temperature drops from ~98° C. to ~92° C.

TABLE 1

| Example | 2.1.2 Adduct (g) | Maleic Anhydride (g) | HQ (ppm)* | $H_2SO_4$ (ppm)* | PO (ml) | Reaction Time (hrs) @ 185° C. | Crude Yield* (%) |
|---|---|---|---|---|---|---|---|
| CE1 | 104 | 21.2 | 0 | 0 | 150 | 6.5 | 23 |
| CE2 | 104 | 21.2 | 12000 | 0 | 150 | 6.5 | 0 |
| CE3 | 208 | 42.4 | 12000 | 0 | 300 | 2.5 | 7.3 |
| CE4 | 208 | 42.4 | 12000 | 0 | 300 | 9.0 | 0 |
| CE5 | 208 | 42.4 | 12000 | 0 | 300 | 8 | 0 |
| E1 | 208 | 42.4 | 12000 | 1500 | 300 | 4.5 | 56 |
| E2 | 208 | 42.4 | 12000 | 1500 | 300 | 3.5 | 62 |
| E3 | 208 | 42.4 | 3000 | 3000 | 300 | 4.5 | 68 |
| E4 | 208 | 42.4 | 10000 | 3000 | 300 | 4.25 | 60 |
| E5 | 208 | 46.6 | 3000 | 3000 | 300 | 4.0 | 80 |
| E6 | 208 | 46.6 | 3000 | 3000 | 300 | 4.25 | 80 |
| E7 | 208 | 50.0 | 3000 | 3000 | 300 | 4.75 | 82 |
| E8 | 208 | 55.0. | 3000 | 3000 | 300 | 4.25 | 90 |
| E9 | 208 | 50.0 | 1250 | 1250 | 300 | 4.5 | 79 |
| E10 | 208 | 46.6 | 3600 | 3600 | 300 | 4.5 | 92 |
| E11 | 208 | 46.6 | 3600 | 3600 | 300 | 5 | 85 |

*based on the weight of the adduct

If the amount of methylidene malonate recovered is found to be more than anticipated, additional polymerization inhibitors should be added to achieve the aforementioned 10 ppm and 100 ppm levels.

The results of these reactions are shown in Table 1 as well. As is evident, the presence of the both the anionic and free radical polymerization inhibitors resulted in markedly improved yields. The crude yield was found, by gas chromatography and mass spectroscopy, to be a combination of the desired 2.1.2 monomer as well as minimal amounts, generally less than about 5% total, of diethyl methylidene (the 2.2 monomer) and di-(ethylmethyl)methylidene (the 2.1.1.2 monomer). Purer materials, 100% pure or nearly so, are readily attained through redistillation.

Examples E12-E17

A second series of experiments were performed, this time using tricresyl phosphate instead of paraffin oil as the reaction medium. The identity and quantity of reactants and solvent medium added to the reactor vessel for conducting the stripping reaction were as set forth in Table 2. Table 2 also identifies the various levels at which the anionic polymerization inhibitor (sulfuric acid) and the free radical polymerization inhibitor (hydroquinone (HQ)) were added. The former was typically added after the other components had been well mixed. Thereafter, the reactor was heated to 185° C. and the temperature held, and the reactor contents allowed to react for the period specified in Table 2.

TABLE 2

| Example | 2.1.2 Adduct (g) | Maleic Anhydride (g) | HQ (ppm)* | $H_2SO_4$ (ppm)* | TCP (ml) | Reaction Time (hrs) @ 185° C. | Crude Yield* (%) |
|---|---|---|---|---|---|---|---|
| E12 | 208 | 42.4 | 3000 | 3000 | 300 | 4.24 | 79 |
| E13 | 208 | 46.6 | 3000 | 3000 | 300 | 3.5 | 82 |
| E14 | 208 | 46.6 | 3000 | 3000 | 300 | 3.5 | 69 |
| E15 | 208 | 50.0 | 3000 | 3000 | 300 | 3.5 | 72 |
| E16 | 832 | 200 | 3000 | 3000 | 1000 | 3.5 | 76 |
| E17 | 832 | 200 | 3000 | 3000 | 250 | 3.5 | 74 |

*based on the weight of the adduct

The initial distillation and redistillation processes and conditions were the same as set forth above for Examples E1-E11. Surprisingly, however, it was found that, unlike paraffin oil, no or only an insignificant amount of tricresyl phosphate carried over into the distillate. Consequently, no separation and washing of the crude product distillate was necessary and these steps were eliminated from this series of experiments. The results attained by this process were as indicated in Table 2.

Examples E18-E20, Comparative Example CE6

To demonstrate the benefit of trifluoroacetic acid (TFA) as a suitable polymerization inhibitor for the methylidene malonates, a series of samples were prepared with and without the addition of trifluoroacetic acid to a redistilled fraction of the 2.1.2 monomer produced in accordance with the present application. The formulation and test results are shown in Table 3.

TABLE 3

| Example | TFA (ppm) | Fixture on Glass (sec) 3% TBAF in acetone | Total Acid Determination (sec) 3% TBAF in DBP | 82° C. Stability (days) No primer |
|---|---|---|---|---|
| CE6 | 0 | 2 | 5 | <2 |
| E18 | 5 | 4 | 10 | 14 |
| E19 | 10 | 10 | 17 | 14 |
| E20 | 15 | 6 | 23 | 14 |

Fixture on Glass was determined by washing two glass slides with acetone and air drying. A 3% solution of tetrabutyl ammonium fluoride (TBAF) in acetone was applied to each slide using a cotton swab and allowed to air dry. Two drops of the monomer formulation was then applied side-by-side in the center of one slide and the other slide placed over the first slide at a right angle and the two held with moderate finger pressure. Fixture time was that time after which a moderate positive pressure could be applied before the glass slides could move relative to one another.

Total Acid Determination was determined by placing 0.1 ml of a 3% solution of tetrabutyl ammonium fluoride (TBAF) in dibutylphthalate in clean test tubes. 0.5 ml of the monomer formulation was then added and the mixture stirred with a stick applicator until the stick was trapped in the cured adhesive and could no longer move.

82° C. Stability was determined by placing a quantity of the monomer into clean 10 mm×75 mm glass test tubes (VWR 89000-476) to a point about 1.75" from the top. Each test tube was capped with a cork stopper and the test tubes placed in an oven at 82° C. One test tube was removed and tilted every hour and then day to test for flow. Cure was said to occur when no flow was seen.

Examples E21-E26

A second series of experiments were conducted using the same fraction of the 2.1.2 monomer as used in Examples E18-E20 but now stabilized with 15 ppm TFA and 1000 ppm hydroquinone. In this experiment the samples were subject to different autoclaving conditions, conditions similar to what may be seen in a product intended for medical applications. A counterpart sample of each was maintained at room temperature for control purposes. The results are shown in Table 4.

TABLE 4

| Example | Test Conditions | Fixture on Glass (sec) 3% TBAF in Acetone | Film Formation (sec) 3% TBAF in Acetone | Total Acid Determination (sec) 3% TBAF in DBP | Color |
|---|---|---|---|---|---|
| E21 | 135° C. for 1 hr | 10 | 110 | 13 | Clear |
|  | RT Control | 12 | 110 | 12 | Clear |
| E22 | 135° C. for 2 hrs | 11 | 95 | 14 | Clear |
|  | RT Control | 13 | 118 | 13 | Clear |
| E23 | 150° C. for 1 hr | 11 | 113 | 14 | Clear |
|  | RT Control | 12 | 118 | 14 | Clear |
| E24 | 150° C. for 2 hrs | 10 | 109 | 15 | Clear |
|  | RT Control | 12 | 100 | 14 | Clear |
| E25 | 186° C. for 1 hr | 15 | 100 | 12 | Clear |
|  | RT Control | 14 | 113 | 10 | Clear |
| E26 | 186° C. for 2 hrs | 10 | 108 | 13 | Clear |
|  | RT Control | 15 | 110 | 12 | Clear |

Fixture and Total Acid Determinations were determined as set forth in the preceding examples. Film formation was determined by cleaning a glass slide with acetone and applying the primer to the surface thereof with a cotton swab. The primer was allowed to air dry following which approximately 0.1 ml of the adhesive material was applied to the primed surface in a bead measuring approximately 9 cm long, 1 cm wide and 3 to 6 mils thick. Cure was considered when a hard, non-tacky surface to the adhesive bead was established.

As seen from Table 4 a negligible effect, if any, was seen on the cure and stability of the adhesive formulations following autoclaving.

Example 27(A) and (B)

(A) 1264 g of the 2.1.2 anthracene adduct, 400 g maleic anhydride, 1.95 g hydroquinone and 1.95 g sulfuric acid were charged to a reactor vessel and heated. The reaction was allowed to continue for 2.5 hours once the pot temperature reached 185° C. The crude reaction product was allowed to cool before being subject to vacuum distillation. Vacuum distillation was supplemented with a trifluoroacetic acid sweep by bubbling ¼% trifluoroacetic acid in 2.1.2 monomer (0.4 cc every 2 minutes) through the system once a pot temperature of 107° C. was reached. Crude distillation yielded 595.5 g of product for a 63.47% yield.

(B) 1664 g of the 2.1.2 anthracene adduct, 400 g maleic anhydride, 1.95 g hydroquinone and 1.95 g sulfuric acid were charged to a reactor vessel and heated. The reaction was allowed to continue for 2.25 hours once the pot temperature reached 185° C. The crude reaction product was allowed to cool before being subject to vacuum distillation. Again vacuum distillation was supplemented with a trifluoroacetic acid (TFAA) sweep by bubbling ¼% trifluoroacetic acid in 2.1.2 monomer (0.4 cc per min) through the system once a pot temperature of 160° C. was attained. Crude distillation yielded 585.77 g of product for a 62.4% yield.

The crude distillation product from (A) and (B) were combined up-stabilized with 1.17 g hydroquinone and 0.6675 g sulfuric acid. The combined material was then subjected to fractional distillation, again with the with the TFAA sweep, with the collection vessels each being prestabilized with 0.66 g or 4540 ppm solution of trifluoroacetic acid. Prestabilization was done by adding the stabilizer solution to the vessel, coating the interior surface with the solution and then dumping the excess and promptly sealing the vessel. Six fractions were obtained and each was further up-stabilized with hydroquinone to a level of 1000 ppm. The following fractions were collected:

Fraction 1: 95-105° C. @ 6.3-2.16 mm, yield: 213.46 g.
Fraction 2: 105-124° C. @ 2.16-3.4 mm, yield: 206.73 g.
Fraction 3: 125-129° C. @ 3.4-3.8-3.7 mm, yield: 217.14 g.
Fraction 4: 129° C. @ 3.7-4.0 mm, yield: 238.11 g.
Fraction 5: 129-130-122° C. @ 4.0-4.3-3.5 mm, yield: 204.41 g.
Fraction 6: yield 33.6 g.

Fractions 2, 3, 4 and 5 where then combined and up-stabilized with 0.85 g hydroquinone and 0.0104 g sulfuric acid. This stabilized distillate was then subjected to a third distillation with the collection vessels each treated with 0.5 g of 4540 ppm TFAA in 2.1.2 monomer stock solution. This fractional distillation resulted in five sub-fractions, including the still bottoms, of 111.13 (SF1), 194.56 (SF2), 177.86 (SF3), 224.44 (SF4) and 131.85 (SF5) g, respectively. Hydroquinone was added to each fraction to bring its level up to 1000 ppm. Analysis of sub-fractions SF3 and SF4 showed purities of 98.8 and 98.7, respectively.

Example 28

An additional adduct process was run using 3377 g of the 2.1.2 anthracene adduct, 800 g maleic anhydride, 4 g hydroquinone and 4 g sulfuric acid (added @ a reaction temp of 138° C.). This reaction gave an exotherm to 195° C. and solids precipitation at 65 minutes. 1617.4 g of crude 2.1.2 methylidene malonate (85% crude yield) with a GC area corresponding to the 2.1.2 monomer of 92.4%. The crude product was refrigerated at 2-8° C. until distillation. Distillation was conducted by adding the crude 2.1.2 methylidene malonate to a 3 L still pot with cooling water set at 10° C. The pot was then stabilized with hydroquinone and sulfuric acid to a final concentration of 1000 ppm HQ and 15 ppm sulfuric acid based on the weight of the crude 2.1.2 monomer. The system is subjected to a trifluoroacetic acid vapor sweep and then placed under vacuum with the pot charged at room temperature to degas and hold it for a minimum of 30 minutes. Each of the collection vessels is pre-rinsed with a solution if 6100 ppm trifluoroacetic acid in toluene, the excess liquid is poured out followed by the addition of 0.10 g HQ and then stoppered to prevent any evaporation of the residual TFA/toluene. (This amount is appropriate for 100 g monomer). The pot is then heated and maleic anhydride distilled off at a pot temperature range of 50-110° C. and a head temperature range of 45-100° C. Maleic anhydride may freeze on the internal surfaces of the condenser. The heat source is then removed and the system vented with nitrogen. The circulating coolant is then raised in temperature to allow the frozen maleic anhydride to melt. The system is then cleaned, reassembled and a vacuum pulled.

The coolant is returned to 10° C. and heat applied to the pot to initiate distillation. The distillate is collected as part of fraction 1 until it is observed to be water white. At this point a new pre-stabilized collection vessel is attached and the fractions collected. Each fraction is then weighed and up-stabilized to final achieve final concentrations of 30 ppm TFA and 1000 ppm HQ. The resultant product fractions were as presented in Table 5.

Example 29

A further example was run using 3300 g of the 2.1.2 anthracene adduct, 793.3 g maleic anhydride, 3.87 g hydroquinone and 3.87 g sulfuric acid (added @ a reaction temp of 113° C.). This reaction gave 1799.7 g of crude 2.1.2 methylidene malonate (96.7% crude yield) with a GC area corresponding to the 2.1.2 monomer of 87.6%. The crude product was refrigerated at 2-80 C until distillation. The crude product was subsequently distilled in accordance with the method set forth in Example 28, with appropriate adjustment of the amount of stabilizers to achieve the same ppm levels for the amount of 2.1.2 monomer. The resultant product fractions were as presented in Table 5

Example 30

The second fractions from the distillations of Examples 28 and 29 were combined and subjected to a second distillation, again following the procedure of Example 28. Here Fraction 2 was collected at a pot temperature range of 105-125° C. and a head temperature of 90-110° C. and a vacuum of, typically, 0.3-0.6 mmHg. Fraction 3 was collected at a pot temperature range of 120-130° C. and a head temperature of 110-115° C. Fraction 3 is continued to collect until a sharp rise in temperature is noted (2-3° C./min) and the distillation is then terminated and the fractions stabilized as appropriate. The resultant products were as presented in Table 5.

TABLE 5

| Example - Fraction | Wt. (g) | Pot Temp (0 C.) | Head Temp (0 C.) | Vacuum (mmHg) | EG* | 2.2 MM | 2.1.2 MM | 2.2 + 2.1.2** | 2.1.2 HPLC |
|---|---|---|---|---|---|---|---|---|---|
| | | | | | | GC area | | | |
| 41 - C | 1617.4 | N/A | N/A | N/A | ND | 4.0 | 91.5 | 95.5 | 95.11 |
| 41 - 1 | 152.8 | RT-121 | RT-109 | 4.5-0.1 | ND | 24.6 | 56.0 | 80.6 | NA |
| 41 - 2 | 521.4 | 121-142 | 109-112 | 0.1-0.5 | 0.5 | 0.5 | 99.0 | 99.5 | 90.97 |
| 41 - 3 | 134.5 | 142-153 | 110-113 | 0.5-0.1 | 0.5 | ND | 98.7 | 98.7 | NA |
| 41 - R | NA | N/A | N/A | N/A | 93.4 | ND | 3.8 | 3.8 | NA |
| 42 - C | 1786.6 | N/A | N/A | N/A | 3.0 | 4.2 | 87.6 | 91.8 | NA |
| 42 - 1 | 154 | RT-128 | RT-107 | 0.3-1.0 | 3.2 | 4.2 | 87.4 | 91.6 | NA |
| 42 - 2 | 621 | 128-136 | 107-110 | 0.6-0.3 | 1.4 | 1.8 | 96.9 | 98.7 | NA |
| 42 - R | NA | N/A | N/A | N/A | NA | NA | NA | NA | NA |
| 43 - 1 | 18.8 | 20-105 | RT-93 | 3.5-0.2 | 6.2 | 31.9 | 48.4 | 80.3 | NA |
| 43 - 2 | 80.8 | 105-121 | 93-110 | 0.2-0.25 | 1.6 | 9.1 | 88.4 | 97.5 | NA |
| 43 - 3 | 865.1 | 121-130 | 109-115 | 0.2-0.6 | 1.3 | 0.2 | 98.1 | 98.3 | NA |
| 43 - R | 75 | N/A | N/A | N/A | NA | NA | NA | NA | NA |

C—crude, R—pot residue, NA—not available, N/A—not applicable, ND—none detected
*Ethyl glycolate;
**total active monomer content While the present invention has been described with respect to aforementioned specific embodiments and examples, it should be appreciated that other embodiments utilizing the concept of the present invention are possible without departing from the scope of the invention. The present invention is defined by the claimed elements and any and all modifications, variations, or equivalents that fall within the spirit and scope of the underlying principles embraced or embodied thereby.

We claim:

1. An improved process for the production of methylidene malonates which process comprises stripping the methylidene malonate from a malonate adduct, wherein the improvement comprises the addition of a reaction phase stabilizer system to the malonate adduct concurrent with or prior to the stripping step, said reaction phase stabilizer system comprising at least one liquid phase primary anionic polymerization inhibitor, alone or in combination with at lease one free radical polymerization inhibitor.

2. The improved process of claim 1 wherein the reaction phase stabilizer system comprises at least one free radical polymerization inhibitors.

3. The improved process of claim 2 wherein the primary anionic polymerization inhibitor is a strong acid.

4. The improved process of claim 1 wherein the one or more primary anionic polymerization inhibitors is selected from sulfuric acid, nitric acid, perchloric acid, maleic acid, trifuoroacetic acid, trichloroacetic acid, hydrochloric acid, hydrobromic acid, benzene sulfonic acid, methane sulfonic acid, trifluoromethane sulfonic acid, fluorosulfonic acid, chlorosulfonic acid, paratoluene sulfonic acid, and chlorosulfonic acid.

5. The improved process of claim 1 wherein the primary anionic polymerization inhibitor is selected from trifluoroacetic acid, sulfuric acid, maleic acid, perchioric acid and chlorosulfonic acid.

6. The improved process of claim 1 wherein the reaction phase stabilizer system comprises a dual liquid-vapor phase primary anionic polymerization inhibitor alone or in combination with a second primary anionic polymerization inhibitor; provided that the combination must be present if the former quickly volatilizes from the reaction mixture under the stripping conditions.

7. The improved process of claim 1 wherein the reaction phase stabilizer system comprises a combination of at least one primary anionic polymerization inhibitor, at least one secondary anionic polymerization inhibitors and at least one free radical polymerization inhibitors.

8. The improved process of claim 1 wherein the malonate adduct is a diene or polynuclear aromatic platform on which the methylidene malonate is formed.

9. The improved process of claim 1 which further comprises the formation of the malonate adduct, wherein the reaction phase stabilizer system is added following isolation of the malonate adduct.

10. The improved process of claim 9 wherein the malonate adduct is formed by the reaction of a malonic acid ester with formaldehyde or a formaldehyde source and a diene in the presence of a catalyst and suitable reaction medium.

11. The improved process of claim 1 further comprising the step of isolating the liquid crude methylidene malonate from the non-liquid components and adding additional reaction phase stabilizer or a separation phase stabilizer to the isolated liquid crude methylidene malonate.

12. The improved process of claim 11 wherein the isolation of the liquid crude methylidene malonate is accomplished by a crude distillation.

13. The improved process of claim 1 wherein the stripping step is a non-pyrolytic stripping process.

14. The improved process of claim 1 wherein the stripping step is a reverse Diels-Alder reaction.

15. The improved process of claim 1 which process includes the step of separating or isolating the stripped methylidene malonate wherein the improvement further comprises the addition of a separation phase stabilizer system to the separated or isolated methylidene malonate material.

16. The improved process of claim 15 wherein the separation phase stabilizer system comprises at least one primary anionic polymerization inhibitor, at least one secondary anionic polymerization inhibitor, or a combination thereof and at least one free radical polymerization inhibitor.

17. An improved process for the production of methylidene malonate from a malonate adduct comprising a methylidene malonate intermediate on an adduct platform wherein the improvement comprises:
  a) stripping the methylidene malonate intermediate from the platform in the presence of a reaction phase stabilizer system to form a crude methylidene malonate product,
  b) adding a reaction phase stabilizer system or a separation phase stabilizer system to the crude methylidene malonate product, and
  c) isolating or purifying or both isolating and purifying the crude methylidene malonate product or any partially purified methylidene malonate product, in the presence of a separation phase stabilizer system, said reaction phase stabilizer system comprising at least one liquid phase primary anionic polymerization inhibitor, alone or in combination with at lease one free radical polymerization inhibitor and said separation phase stabilizer system comprising at least one liquid phase primary or secondary anionic polymerization inhibitors, or both, alone or in combination with at least one free radical polymerization inhibitor.

18. The improved process of claim 17 which further comprises the formation of the malonate adduct, wherein the reaction phase stabilizer system is added following isolation of the malonate adduct from its reaction mixture.

19. The improved process of claim 18 wherein the malonate adduct is formed by the reaction of a malonic acid ester with formaldehyde or a formaldehyde source and a diene in the presence of a catalyst and suitable reaction medium.

20. The improved process of claim 17 wherein the reaction phase stabilizer system is added to the malonate adduct prior to or concurrent with the stripping process.

21. The improved process of claim 17 wherein the separation phase stabilizer system is added to the material to be purified prior to or concurrent with the purification process.

22. The improved process of claim 21 wherein the separation phase stabilizer system is also added to the purified or partially purified methylidene malonate resulting from the purification process.

23. The improved process of claim 17 wherein at least a portion of the separation phase stabilizer is added to the collection vessel for the isolated or purified methylidene malonate before initiating the isolation or purification process.

24. The improved process of claim 17 wherein the isolation or purification process comprises a sequence of at least two distillations on the crude methylidene malonate product with the first distillation comprising the separation of a liquid crude methylidene malonate from any non-liquid components in the crude methylidene malonate product and the second distillation comprising a re-distillation of the product of the first distillation.

25. The improved process of claim 17 wherein the isolation or purification process comprises a sequence of at least three distillations on the crude methylidene malonate product with the first distillation comprising the separation of a liquid crude methylidene malonate from any non-liquid components in the crude methylidene malonate product, the second distillation comprising a re-distillation of the product of the first distillation and the third or subsequent distillation comprising the distillation of those fractions from the preceding distillation containing at least 50% by weight of methylidene malonate.

26. The improved process of claim 17 wherein a liquid crude methylidene malonate is separated any non-liquid components of the crude methylidene malonate product and said separation is by a method other than distillation and wherein the method further comprises one or more additional purification steps, at least one of which is a distillation step.

27. The improved process of claim 17 wherein the stripping step is a non-pyrolytic stripping process.

28. The improved process of claim 17 wherein the stripping step is a reverse Diels-Alder reaction.

29. The improved process of claim 17 wherein the reaction phase stabilizer system further comprises a secondary anionic polymerization inhibitor.

30. The improved process of claim 17 wherein both the reaction phase stabilizer system and the separation phase stabilizer system contain at least one free radical polymerization inhibitor.

31. The improved process of claim 17 wherein the primary anionic polymerization inhibitor comprises a strong acid which is characterized as having a pKa of about 2 or less and the secondary anionic polymerization inhibitor is characterized as being an anionic polymerization inhibitor other than a primary anionic polymerization inhibitor.

32. The improved process of claim 17 wherein the one or more primary anionic polymerization inhibitors is selected from sulfuric acid, nitric acid, perchloric acid, maleic acid, trifuoroacetic acid, trichloroacetic acid, hydrochloric acid, hydrobromic acid, benzene sulfonic acid, methane sulfonic acid, trifluoromethane sulfonic acid, fluorosulfonic acid, chlorosulfonic acid, paratoluene sulfonic acid, and chlorosulfonic acid.

33. The improved process of claim 17 wherein the at least one anionic polymerization inhibitor is or includes trifluoroacetic acid, sulfuric acid, maleic acid, perchloric acid or chlorosulfonic acid.

34. The improved process of claim 17 wherein i) the at least one primary anionic polymerization inhibitor of the reaction phase stabilizer system is a dual liquid-vapor phase primary anionic polymerization inhibitor or a combination thereof with a second liquid phase primary anionic polymerization inhibitor; provided that the combination must be present if the former quickly volatilizes from the reaction mixture under the stripping conditions or ii) the at least one primary or secondary anionic polymerization inhibitor of the separation phase stabilizer system is a dual liquid-vapor phase primary or secondary anionic polymerization inhibitor, or both, or a combination thereof with a second liquid phase primary or secondary anionic polymerization inhibitor provided that the combination must be present if the dual liquid-vapor phase anionic polymerization inhibitor quickly volatilizes from crude or partially purified methylidene malonate under the purification conditions.

\* \* \* \* \*